US 9,243,603 B2

(12) United States Patent
Martin et al.

(10) Patent No.: US 9,243,603 B2
(45) Date of Patent: Jan. 26, 2016

(54) LASER IGNITION SYSTEM BASED DIAGNOSTICS

(71) Applicant: Ford Global Technologies, LLC, Dearborn, MI (US)

(72) Inventors: Douglas Raymond Martin, Canton, MI (US); Kenneth James Miller, Canton, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 49 days.

(21) Appl. No.: 14/152,851

(22) Filed: Jan. 10, 2014

(65) Prior Publication Data
US 2015/0198136 A1    Jul. 16, 2015

(51) Int. Cl.
| | |
|---|---|
| *G01N 21/00* | (2006.01) |
| *F02P 23/04* | (2006.01) |
| *G01M 15/06* | (2006.01) |
| *G01S 17/06* | (2006.01) |
| *G01S 17/10* | (2006.01) |
| *G01S 17/88* | (2006.01) |
| *F02D 41/00* | (2006.01) |

(Continued)

(52) U.S. Cl.
CPC ............... *F02P 23/04* (2013.01); *F02D 35/022* (2013.01); *F02D 41/009* (2013.01); *F02D 41/22* (2013.01); *G01M 15/06* (2013.01); *G01S 17/06* (2013.01); *G01S 17/10* (2013.01); *G01S 17/88* (2013.01); *G01N 2201/0697* (2013.01); *G01N 2201/06113* (2013.01); *G01S 7/497* (2013.01)

(58) Field of Classification Search
CPC ...... G01B 11/002; G01B 11/04; G01B 11/26; G01B 11/272; G01B 11/026; G01M 15/02; G01M 15/04; G01M 15/042; G01M 15/05; G01M 15/06

USPC ....... 92/5 R; 91/1; 73/114.26–114.29, 114.77
See application file for complete search history.

(56) References Cited

U.S. PATENT DOCUMENTS

| | | | | |
|---|---|---|---|---|
| 4,518,268 | A | * | 5/1985 | Swis ..................... F02B 77/083 374/144 |
| 5,204,490 | A | * | 4/1993 | Soltz et al. .................... 102/201 |

(Continued)

FOREIGN PATENT DOCUMENTS

GB          2441145 A      2/2008

OTHER PUBLICATIONS

Martin, Douglas R. et al., "Laser Ignition and Misfire Monitor," U.S. Appl. No. 13/677,641, filed Nov. 15, 2012, 30 pages.

(Continued)

*Primary Examiner* — Kara E Geisel
*Assistant Examiner* — Hina F Ayub
(74) *Attorney, Agent, or Firm* — Julia Voutyras; Alleman Hall McCoy Russell & Tuttle LLP

(57) ABSTRACT

Methods and systems are provided for using an engine laser ignition system to perform a visual inspection of an engine and diagnose various cylinder components and conditions based on engine positional measurements. Laser pulses may be emitted at a lower power level during an intake and/or exhaust stroke to illuminate a cylinder interior while a photodetector captures images of the cylinder interior. Additionally, laser pulses may be emitted at a higher power level to initiate cylinder combustion while the photodetector captures images of the cylinder interior using the light generated during cylinder combustion.

19 Claims, 13 Drawing Sheets

(51) Int. Cl.
  *F02D 41/22* (2006.01)
  *F02D 35/02* (2006.01)
  *G01S 7/497* (2006.01)

(56) References Cited

U.S. PATENT DOCUMENTS

| | | | | |
|---|---|---|---|---|
| 5,459,940 | A | * | 10/1995 | McKenzie ............ G01M 15/06 33/600 |
| 5,477,771 | A | * | 12/1995 | Black .............................. 92/5 R |
| 5,621,644 | A | * | 4/1997 | Carson et al. ................... 701/102 |
| 6,512,588 | B1 | * | 1/2003 | Hill ................................ 356/510 |
| 6,732,709 | B1 | * | 5/2004 | Havran et al. ............ 123/406.24 |
| 7,334,563 | B2 | | 2/2008 | Mifuji et al. |
| 2003/0159667 | A1 | * | 8/2003 | Armstrong ................ 123/90.16 |
| 2006/0037572 | A1 | | 2/2006 | Yalin et al. |
| 2006/0071289 | A1 | * | 4/2006 | Tanaka et al. ................. 257/432 |
| 2008/0257294 | A1 | * | 10/2008 | Vogel et al. ................ 123/143 B |
| 2009/0030586 | A1 | * | 1/2009 | Bartolomeo et al. ......... 701/102 |
| 2010/0319640 | A1 | * | 12/2010 | Shewell ...................... 123/90.15 |
| 2012/0131927 | A1 | | 5/2012 | Denis et al. |
| 2013/0206108 | A1 | * | 8/2013 | Schule et al. ................. 123/435 |
| 2013/0312601 | A1 | * | 11/2013 | Subrt .............................. 92/5 R |

OTHER PUBLICATIONS

Martin, Douglas R. et al., "Engine With Laser Ignition and Measurement," U.S. Appl. No. 13/689,601, filed Nov. 29, 2012, 44 pages.

Martin, Douglas R. et al., "Engine With Laser Ignition and Measurement," U.S. Appl. No. 13/689,578, filed Nov. 29, 2012, 54 pages.

Martin, Douglas R. et al., "Laser Ignition Safety Interlock System and Method," U.S. Appl. No. 13/870,327, filed Apr. 25, 2013, 30 pages.

Martin, Douglas R. et al., "Laser Ignition System Based Diagnostics," U.S. Appl. No. 14/152,811, filed Jan. 10, 2014, 85 pages.

Martin, Douglas R. et al., "Laser Ignition System Based Diagnostics," U.S. Appl. No. 14/152,833, filed Jan. 10, 2014, 85 pages.

Marshall, L., "Laser Car Ignition Dream Sparks Multiple Approaches," Phototonics, http://www.phototonics.com/Article.aspx?AID=51731, Accessed Apr. 8, 2014, 7 pages.

Martin, Douglas R. et al., "Laser Ignition System Based Diagnostics," U.S. Appl. No. 13/865,088, filed Apr. 17, 2013, 41 pages.

Martin, Douglas R. et al., "Laser Ignition System Based Diagnostics," U.S. Appl. No. 13/865,089, filed Apr. 17, 2013, 40 pages.

\* cited by examiner

LASER IGNITION SYSTEM BASED DIAGNOSTICS

FIELD

The present application relates to methods and systems for diagnosing an engine using components of a laser ignition system.

BACKGROUND AND SUMMARY

Engine system components (such as cylinder valves, crankshafts, camshafts, pistons, fuel injectors etc.) may be intermittently diagnosed for damage incurred during engine operation. Diagnostics may involve visually inspecting the components for damage (e.g., misalignment or twisting), such as by removing a spark plug and obtaining a bore scope to view inside the cylinder. Damage to crankshaft and/or camshafts can lead to variability in determining their position (in order to identify engine and piston positions). As such, the position of the cams/pistons is required during an engine restart to enable coordination of the spark timing and fuel delivery in the engine. Thus, any errors in position determination can lead to reduced ability in achieving and maintaining fast synchronization, reliable combustion, and reduced emissions. Further, any delays in identifying engine position can also delay engine starting.

The inventors herein have recognized that the above discussed approaches for visually inspecting engine components can add extensive time, cost, and complexity to the diagnostics. In particular, most of the above approaches require a skilled technician, complex diagnostic tools, specialized laboratory facilities, and time consuming engine teardown. In view of these issues, the inventors have realized that in engine systems configured with laser ignition capabilities, components of the laser ignition system can be advantageously used to diagnose various engine system components.

In one example, the engine may be diagnosed by a method comprising: over an engine cycle, operating a laser ignition device in each engine cylinder; identifying a piston position in each cylinder based on the operating; and indicating degradation of an engine crankshaft based on a piston position of each cylinder. In another example, a cylinder valve position in each cylinder may be identified based on the operating; and degradation of a camshaft may be indicated based on the valve position of each cylinder. In still a further example, laser illumination based piston position measurements may be used to determine the position of a crankshaft while laser illumination based intake or exhaust valve position measurements may be used to determine the position of a camshaft. Based on the relative positioning of the crankshaft relative to the camshaft, misalignment errors may be identified.

For example, a laser ignition device may be operated at a lower power level during an intake stroke of a cylinder to rapidly direct laser pulses into a cylinder and perform a planar sweep of the cylinder. Based on a duration elapsed since the emission of the laser pulse and the detection of the laser pulse following reflection off the piston surface, the position of the piston in the given cylinder may be determined. In addition, the duration may be used to infer whether a cylinder valve is open or closed. For example, based on the elapsed duration estimated following laser pulse emission in an intake stroke, it may be determined if the intake valve is open or closed, and thereby the position of an exhaust valve may be inferred. Alternatively, based on the elapsed duration estimated following laser pulse emission in an exhaust stroke, it may be determined if the exhaust valve is open or closed, and thereby the position of an intake valve may be inferred. By comparing the piston position of each cylinder relative to one another crankshaft alignment errors may be determined. For example, by comparing the estimated position of each cylinder to the expected position of each cylinder (based on the cylinder firing order, the engine configuration, etc.), it may be determined if the crankshaft position is deviated from a home position, and crankshaft degradation due to twisting or breaking may be indicated. Likewise, by comparing the intake or exhaust valve position of each cylinder relative to one another, camshaft alignment errors may be determined. For example, by comparing the estimated position of each cylinder's intake valve, and thereby intake cam, to the expected position of each cylinder's intake valve and intake cam (based on the cylinder firing order, the engine configuration, the cylinder stroke, etc.), it may be determined if the camshaft position is deviated from a home position, and camshaft degradation due to twisting or breaking may be indicated. Further still, by comparing the estimated crankshaft position to the estimated camshaft position, misalignment errors may be determined.

In this way, engine position based diagnostics can be expedited and simplified without necessitating engine disassembly. In particular, it may be possible to use piston position and cylinder valve position estimates, as determined using an engine laser ignition system, to determine crankshaft and/or camshaft alignment errors. By taking advantage of the laser ignition system to estimate the piston and valve position, positional information can be gathered faster and more reliably. By using the positional information to diagnose the crankshaft and camshaft, the time and cost associated with the visual inspection of the components is reduced. Overall, engine inspection can be simplified without reducing inspection accuracy.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
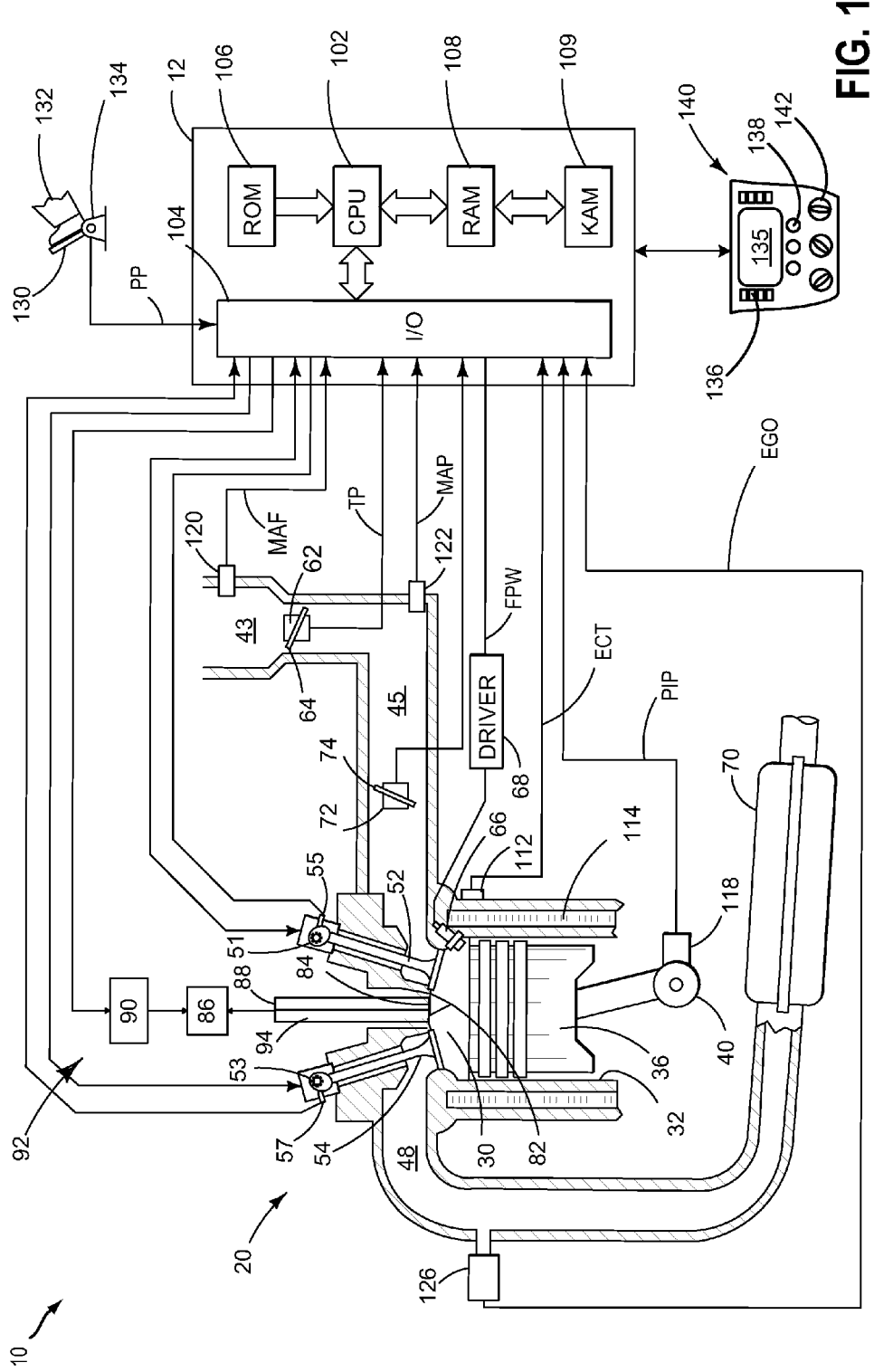
FIG. 1 shows an example combustion chamber of an internal combustion engine coupled in a hybrid vehicle system.
Figure 2:
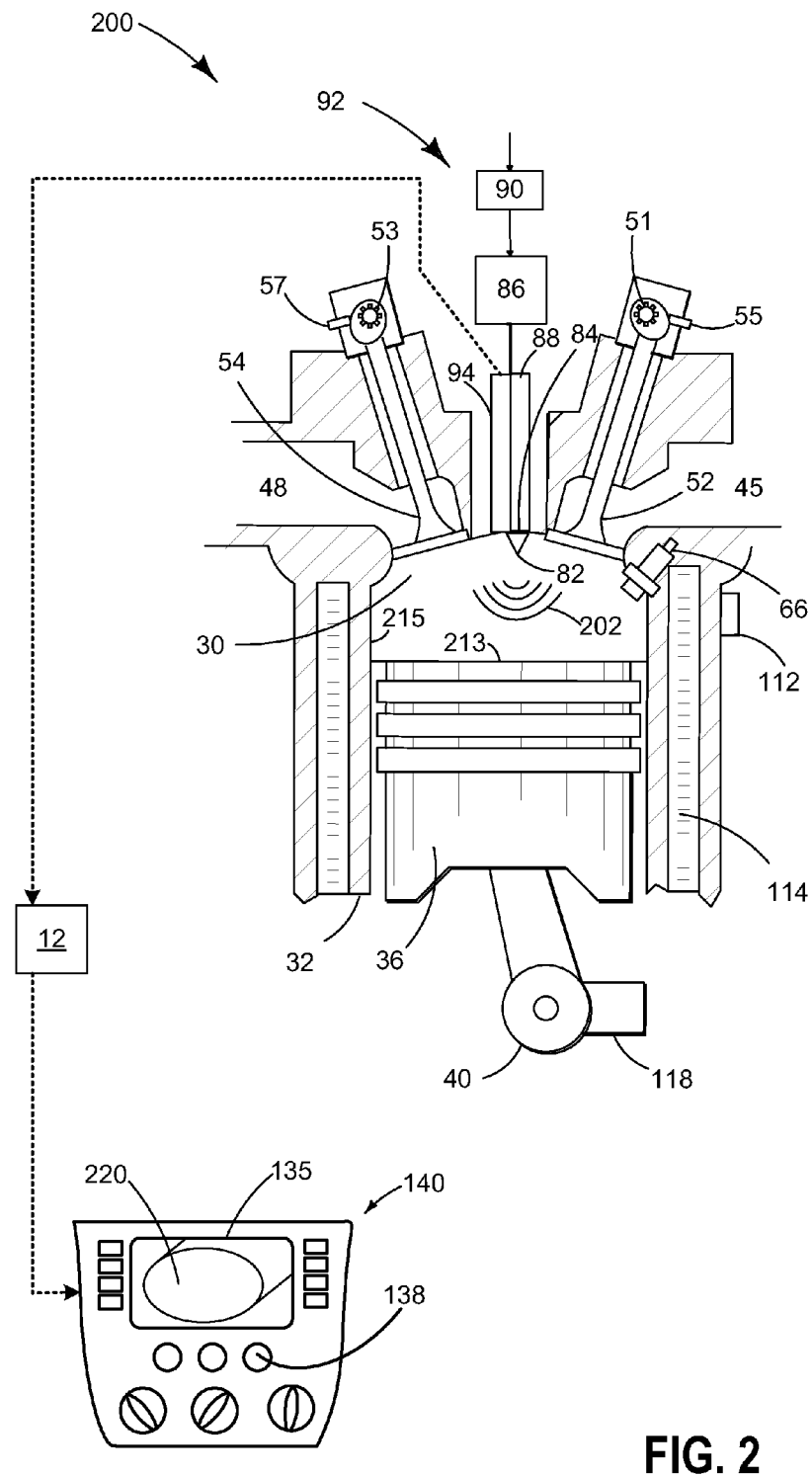
FIG. 2 shows an example of image capture and display using a laser system of the engine of FIG. 1.
Figure 3:
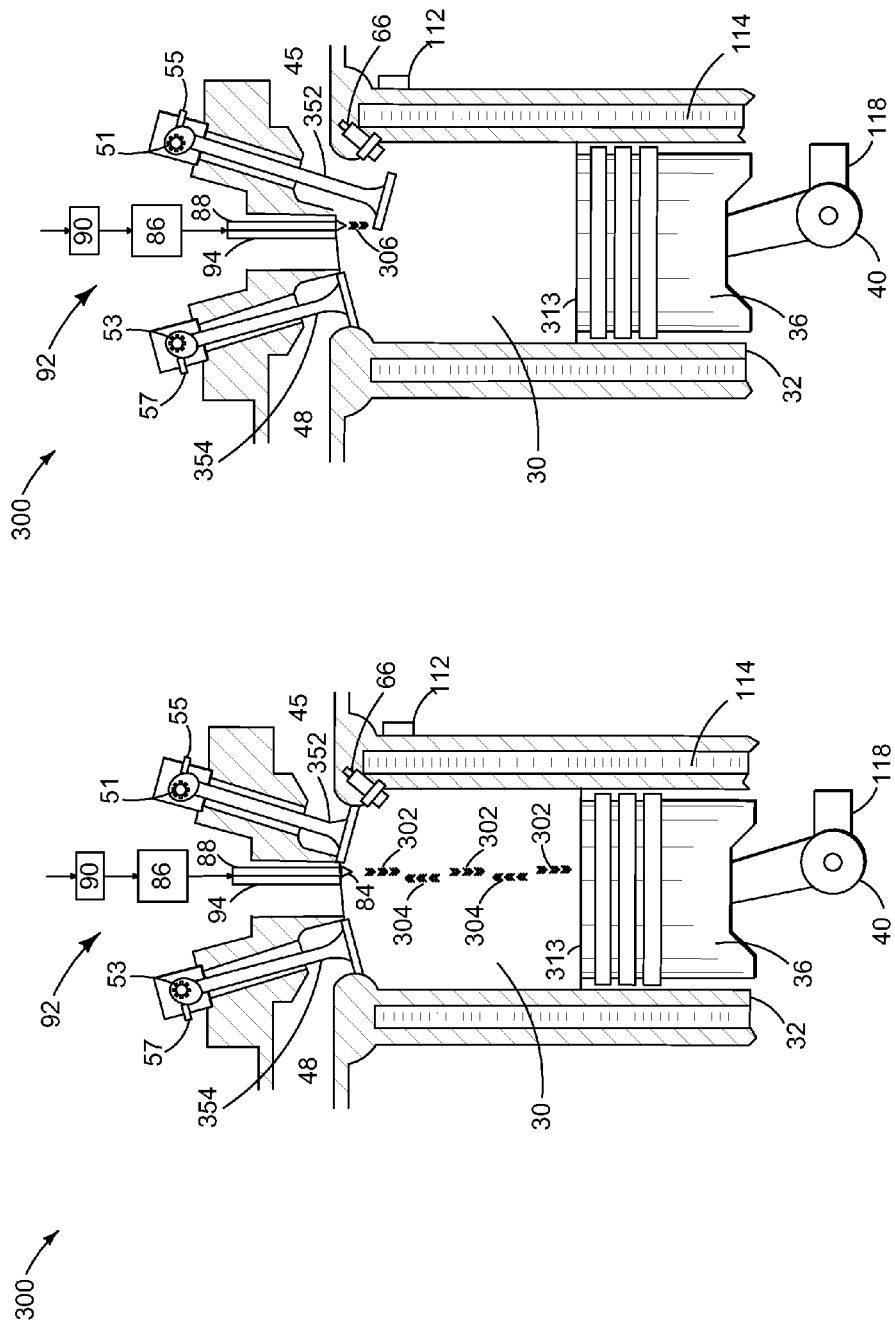
FIGS. 3 A-B show an example of laser light pulse emission to an engine cylinder.
Figure 4:
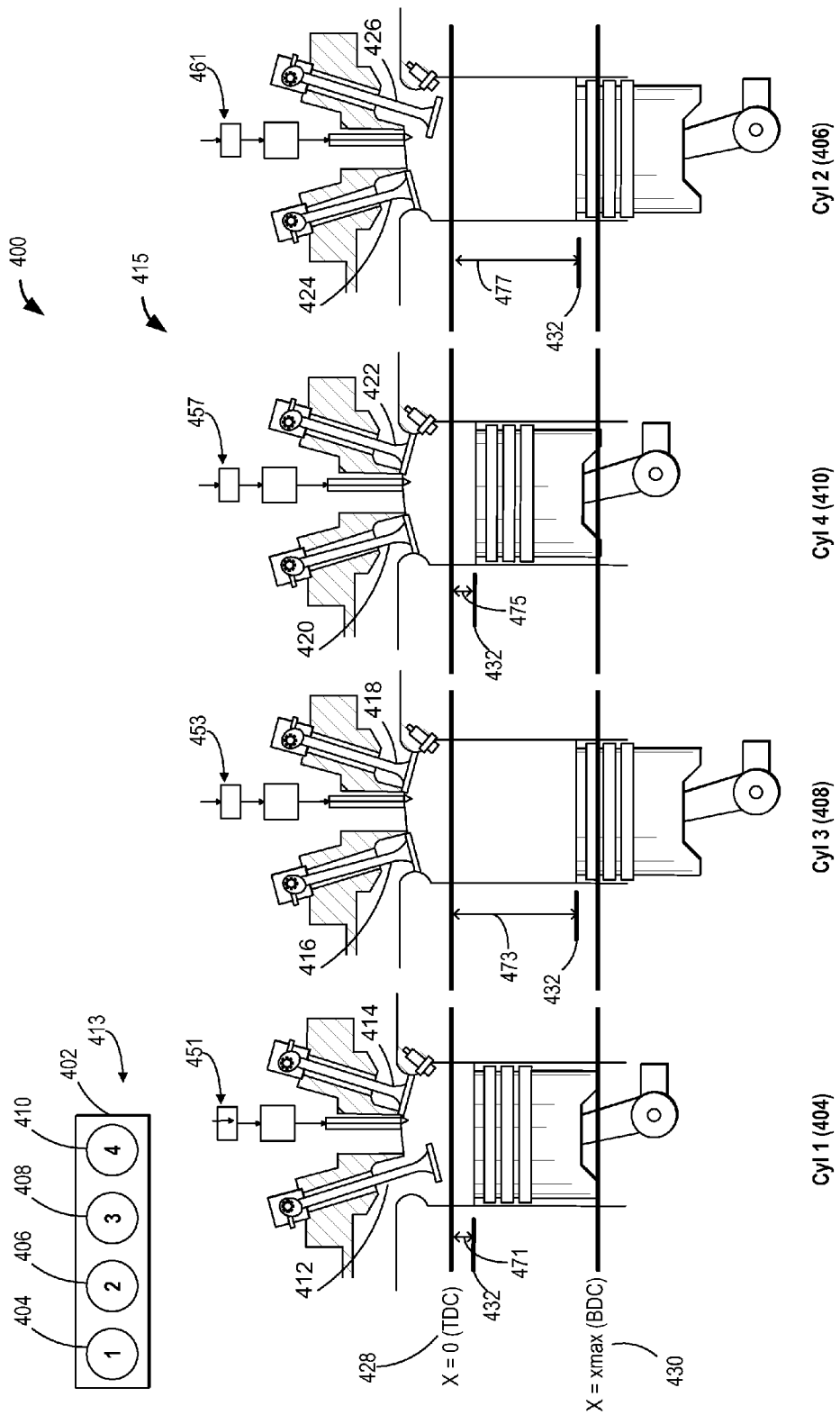
FIG. 4 shows an example four cylinder engine stopped at a random position in its drive cycle.
Figure 5:
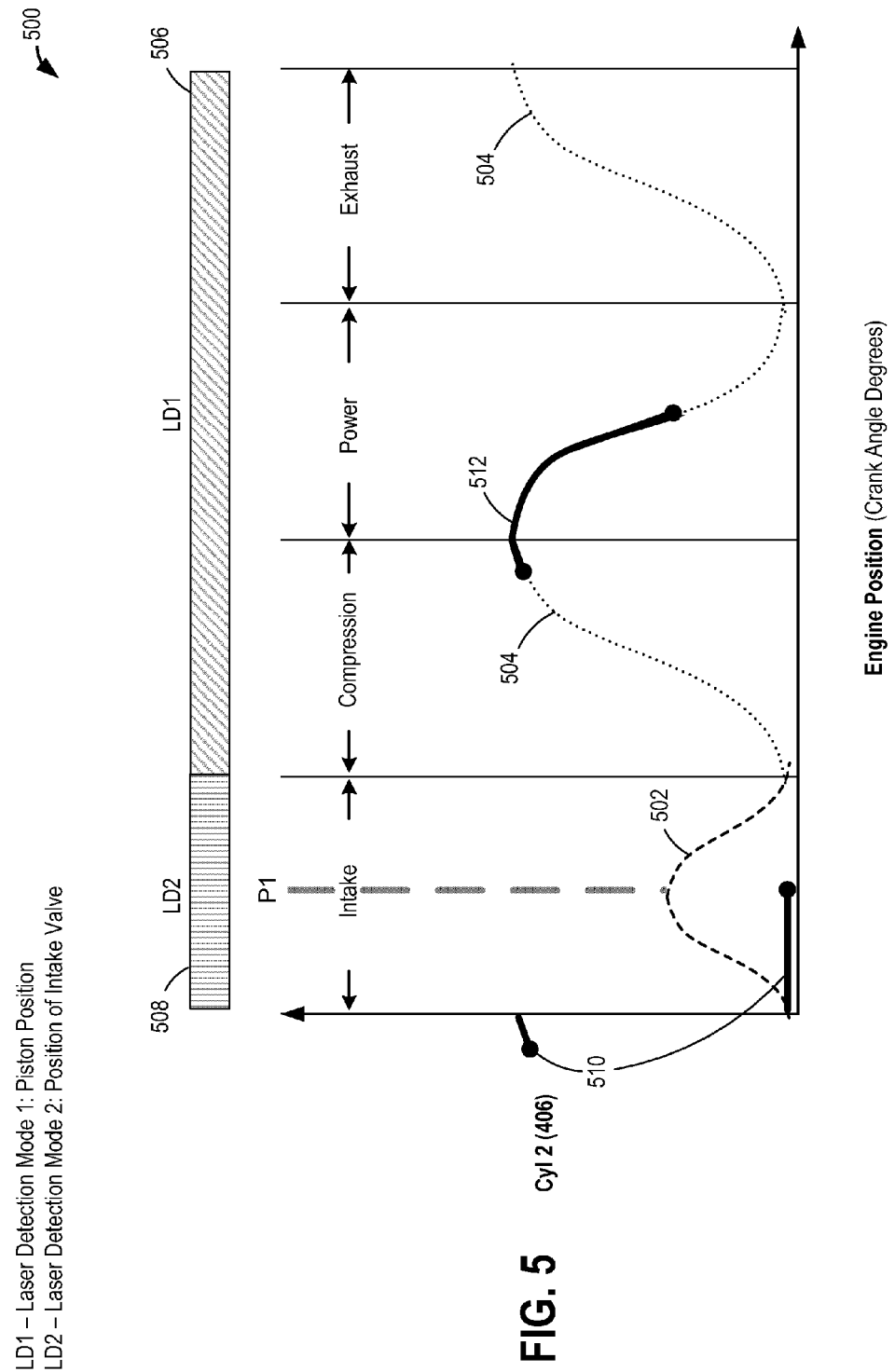
FIG. 5 shows two operational modes of an engine laser ignition system used for identifying piston and intake valve positions of a cylinder during an engine cycle.

Methods and systems are provided for diagnosing one or more engine cylinder components using a laser ignition system, such as shown in FIG. 1. As shown at FIGS. 2-3, laser light pulse emission at lower intensities may be used for illuminating the interior of a cylinder while a photodetector captures in-cylinder images. Laser light pulse emission at higher intensities may also be used for initiating combustion while the light generated during combustion is used by the photodetector to capture images of the interior of the cylinder. The generated images may be used to diagnose various in-cylinder components and cylinder combustion parameters. Further still, cam and piston position determination may be accurately performed using the laser light pulse emission, as shown at FIGS. 4-5 allowing for diagnosis of engine camshafts and crankshafts, as discussed at FIG. 8. An engine controller may be configured to perform a control routine, such as the routine of FIG. 6, to diagnose degradation of one or more cylinder components based on in-cylinder images generated by a photodetector during an intake stroke using light from laser pulse emission. The controller may also perform a control routine, such as the routine of FIG. 7, to diagnose cylinder component degradation based on in-cylinder images generated by a photodetector using light generated during a cylinder combustion event. Example diagnostic methods for selected engine components are elaborated at FIGS. 9-13.

Turning to FIG. 1, an example hybrid propulsion system 10 is depicted. The hybrid propulsion system may be configured in a passenger on-road vehicle. Hybrid propulsion system 10 includes an internal combustion engine 20. The engine may be coupled to a transmission (not shown), such as a manual transmission, automatic transmission, or combinations thereof. Further, various additional components may be included, such as a torque converter, and/or other gears such as a final drive unit, etc. The hybrid propulsion system also includes an energy conversion device (not shown), which may include a motor, a generator, among others and combinations thereof. The energy conversion device may be operated to absorb energy from vehicle motion and/or the engine and convert the absorbed energy to an energy form suitable for storage at an energy storage device. The energy conversion device may also be operated to supply an output (power, work, torque, speed, etc.) to engine 20, so as to augment the engine output. It should be appreciated that the energy conversion device may, in some embodiments, include a motor, a generator, or both a motor and generator, among various other components used for providing the appropriate conversion of energy between the energy storage device and the vehicle drive wheels and/or engine.

Engine 20 may be a multi-cylinder internal combustion engine, one cylinder of which is depicted in detail at FIG. 1. Engine 20 may be controlled at least partially by a control system including controller 12 and by input from a vehicle operator 132 via an input device 130. In this example, input device 130 includes an accelerator pedal and a pedal position sensor 134 for generating a proportional pedal position signal PP.

Combustion cylinder 30 of engine 20 may include combustion cylinder walls 32 with piston 36 positioned therein. Piston 36 may be coupled to crankshaft 40 so that reciprocating motion of the piston is translated into rotational motion of the crankshaft. Crankshaft 40 may be coupled to at least one drive wheel of propulsion system 10 via an intermediate transmission system. Combustion cylinder 30 may receive intake air from intake manifold 45 via intake passage 43 and may exhaust combustion gases via exhaust passage 48. Intake manifold 45 and exhaust passage 48 can selectively communicate with combustion cylinder 30 via respective intake valve 52 and exhaust valve 54. In some embodiments, combustion cylinder 30 may include two or more intake valves and/or two or more exhaust valves.

Engine 20 may optionally include cam position sensors 55 and 57. However, in the example shown, intake valve 52 and exhaust valve 54 may be controlled by cam actuation via respective cam actuation systems 51 and 53. Cam actuation systems 51 and 53 may each include one or more cams and may utilize one or more of cam profile switching (CPS), variable cam timing (VCT), variable valve timing (VVT) and/or variable valve lift (VVL) systems that may be operated by controller 12 to vary valve operation. To enable detection of cam position, cam actuation systems 51 and 53 may have toothed wheels. The position of intake valve 52 and exhaust valve 54 may be determined by position sensors 55 and 57, respectively. In alternative embodiments, intake valve 52 and/or exhaust valve 54 may be controlled by electric valve actuation. For example, cylinder 30 may alternatively include an intake valve controlled via electric valve actuation and an exhaust valve controlled via cam actuation including CPS and/or VCT systems.

Fuel injector 66 is shown coupled directly to combustion cylinder 30 for injecting fuel directly therein in proportion to the pulse width of signal FPW received from controller 12 via electronic driver 68. In this manner, fuel injector 66 provides what is known as direct injection of fuel into combustion cylinder 30. The fuel injector may be mounted on the side of the combustion cylinder or in the top of the combustion cylinder, for example. Fuel may be delivered to fuel injector 66 by a fuel delivery system (not shown) including a fuel tank, a fuel pump, and a fuel rail. In some embodiments, combustion cylinder 30 may alternatively or additionally include a fuel injector arranged in intake passage 43 in a configuration that provides what is known as port injection of fuel into the intake port upstream of combustion cylinder 30.

Intake passage 43 may include a charge motion control valve (CMCV) 74 and a CMCV plate 72 and may also include a throttle 62 having a throttle plate 64. In this particular example, the position of throttle plate 64 may be varied by controller 12 via a signal provided to an electric motor or actuator included with throttle 62, a configuration that may be referred to as electronic throttle control (ETC). In this manner, throttle 62 may be operated to vary the intake air provided to combustion cylinder 30 among other engine combustion cylinders. Intake passage 43 may include a mass air flow sensor 120 and a manifold air pressure sensor 122 for providing respective signals MAF and MAP to controller 12.

Exhaust gas sensor 126 is shown coupled to exhaust passage 48 upstream of catalytic converter 70. Sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), a $NO_x$, HC, or CO sensor. The exhaust system may include light-off catalysts and underbody catalysts, as well as exhaust manifold, upstream and/or downstream air/fuel ratio sensors. Catalytic converter 70 can include multiple catalyst bricks, in one example. In another example, multiple emission control devices, each with multiple bricks, can be used. Catalytic converter 70 can be a three-way type catalyst in one example.

Controller 12 is shown in FIG. 1 as a microcomputer, including microprocessor unit 102, input/output ports 104, an electronic storage medium for executable programs and calibration values shown as read-only memory chip 106 in this particular example, random access memory 108, keep alive memory 109, and a data bus. The controller 12 may receive various signals and information from sensors coupled to engine 20, in addition to those signals previously discussed, including measurement of inducted mass air flow (MAF) from mass air flow sensor 120; engine coolant temperature (ECT) from temperature sensor 112 coupled to cooling sleeve 114; in some examples, a profile ignition pickup signal (PIP) from Hall effect sensor 118 (or other type) coupled to crankshaft 40 may be optionally included; throttle position (TP) from a throttle position sensor; and absolute manifold pressure signal, MAP, from sensor 122. The Hall effect sensor 118 may optionally be included in engine 20 because it functions in a capacity similar to the engine laser system described herein. Storage medium read-only memory 106 can be programmed with computer readable data representing instructions executable by processor 102 for performing the methods described below as well as variations thereof.

Laser system 92 includes a laser exciter 88 and a laser control unit (LCU) 90. LCU 90 causes laser exciter 88 to generate laser energy. LCU 90 may receive operational instructions from controller 12. Laser exciter 88 includes a laser oscillating portion 86 and a light converging portion 84. The light converging portion 84 converges laser light generated by the laser oscillating portion 86 on a laser focal point 82 of combustion cylinder 30. In one example, light converging portion 84 may include one or more lenses.

A photodetector 94 may be located in the top of cylinder 30 as part of laser system 92 and may receive return pulses from the top surface of piston 36. Photodetector 94 may include a camera with a lens. In one example, the camera is a charge coupled device (CCD). The CCD camera may be configured to detect and read laser pulses emitted by LCU 90. In one example, when the LCU emits laser pulses in an infra-red frequency range, the CCD camera may operate and receive the pulses in the infra-red frequency range. In such an embodiment, the camera may also be referred to as an infra-red camera. In other embodiments, the camera may be a full-spectrum CCD camera that is capable of operating in a visual spectrum as well as the infra-red spectrum. The camera may include a lens for focusing the detected laser pulses and generating an image of the interior of the cylinder. In one example, the lens is a fish-eye lens that creates a wide panoramic or hemispherical image of the inside of the cylinder. After laser emission from LCU 90, the laser sweeps within the interior region of cylinder 30 at laser focal point 82. Light energy that is reflected off of piston 36 may be detected by the camera in photodetector 94. Photodetector 94 may also capture images of the interior of the cylinder, as elaborated below.

Laser system 92 is configured to operate in more than one capacity with the timing of each operation based on engine position of a four-stroke combustion cycle. For example, laser energy may be utilized for igniting an air/fuel mixture during a power stroke of the engine, including during engine cranking, engine warm-up operation, and warmed-up engine operation. Fuel injected by fuel injector 66 may form an air/fuel mixture during at least a portion of an intake stroke, where igniting of the air/fuel mixture with laser energy generated by laser exciter 88 commences combustion of the otherwise non-combustible air/fuel mixture and drives piston 36 downward. Furthermore, light generated during the cylinder combustion event may be used by photodetector 94 for capturing images of an interior of the cylinder. As elaborated at FIG. 9, the generated images may then be used to diagnose various in-cylinder components as well as cylinder combustion parameters.

In a second operating capacity, LCU 90 may deliver low powered pulses to the cylinder. The low powered pulses may be used to determine piston and valve position during the four-stroke combustion cycle, as discussed at FIGS. 4-7. The piston position and valve position measurements may then be used to diagnose cylinder components such as camshafts and crankshafts, as discussed at FIG. 10. In addition, upon reactivating an engine from idle-stop conditions, laser energy may be utilized to monitor the position, velocity, etc. of the engine in order to synchronize fuel delivery and valve timing. Furthermore, light generated by the laser light pulse emission at the lower power may be used for capturing images of an interior of the cylinder before a cylinder combustion event occurs, such as during an intake stroke. The images may also be generated during non-combusting conditions, such as when operating in specific diagnostic modes. As elaborated at FIG. 8, the generated images may then be used to diagnose various in-cylinder components.

The images generated at photodetector 94 may be displayed to a mechanic or service technician on a center-console of the vehicle so that they can perform a visual inspection and identify any cylinder component degradation. For example, the laser ignition device, coupled to photodetector 94, may transmit light pulses into cylinder 30 while photodetector 94, including an infrared camera equipped with a fish-eye lens, generates images that are transmitted wirelessly to an engine controller and viewed on the display of the vehicle. In some examples, as discussed with reference to FIG. 2, while operating the laser ignition device, an operator controlled knob on the center-console can adjust the engine position. These adjustments include turning the engine forwards or backwards from an initial engine position allowing for further inspection of the cylinder for an indication of degradation.

LCU 90 may direct laser exciter 88 to focus laser energy at different locations depending on operating conditions. For example, the laser energy may be focused at a first location away from cylinder wall 32 within the interior region of cylinder 30 in order to ignite an air/fuel mixture. In one embodiment, the first location may be near top dead center (TDC) of a power stroke. Further, LCU 90 may direct laser exciter 88 to generate a first plurality of laser pulses directed to the first location, and the first combustion from rest may receive laser energy from laser exciter 88 that is greater than laser energy delivered to the first location for later combustions. As another example, the laser energy may be focused at a second location towards the cylinder wall closest to the intake port of the cylinder in order to diagnose an injector spray pattern or an intake air flow pattern.

Controller 12 controls LCU 90 and has non-transitory computer readable storage medium including code to adjust the location of laser energy delivery based on temperature, for example the ECT. Laser energy may be directed at different locations within cylinder 30. Controller 12 may also incorporate additional or alternative sensors for determining the operational mode of engine 20, including additional temperature sensors, pressure sensors, torque sensors as well as sensors that detect engine rotational speed, air amount and fuel injection quantity. Additionally or alternatively, LCU 90 may directly communicate with various sensors, such as temperature sensors for detecting the ECT, for determining the operational mode of engine 20.

As described above, FIG. 1 shows one cylinder of multi-cylinder engine 20, and each cylinder may similarly include its own set of intake/exhaust valves, fuel injector, laser ignition system, etc.

FIG. 2 illustrates an example embodiment 200 of how the laser system 92 (of FIG. 1) may emit laser pulses into cylinder 30 so that a photodetector of the laser system can capture images of the interior of the cylinder. The images may be displayed to a vehicle operator to enable visual inspection of the cylinder for damage. As such, components already introduced in FIG. 1 are not re-introduced in FIG. 2.

FIG. 2 shows laser system 92 that includes laser exciter 88, photodetector 94 and LCU 90. LCU 90 causes laser exciter 88 to generate laser energy. High frequency laser pulses are directed towards various locations of the cylinder to scan as much of the cylinder as possible. For example, laser pulses 202 may be directed towards cylinder walls 215, interior of cylinder 30, piston top surface 213 and inner surface of valves 52 and 54 (that is, the surface facing the cylinder). By scanning as much of the cylinder as quickly as possible, laser pulse 202 acts as a wide beam light source or light bulb enabling photodetector 94 (in particular, the CCD camera) to capture images 220 of the interior of the cylinder. As such, when operating as a light source for image capture during diagnostics, the laser ignition system (or laser device) may be considered to be operating in a projector or illuminator mode, and LCU 90 may receive operational instructions, such as a power mode, from controller 12. When operating in selected diagnostic modes, the laser system 92 emits a series of low power pulses at high frequency. In comparison, during ignition, the laser may be pulsed quickly with high energy intensity to ignite the air/fuel mixture. In one example, during the diagnostic mode, the laser may be pulsed at the low energy level with a frequency-modulation having a repetitive linear frequency ramp. The low power frequent laser pulses may be emitted in the infra-red spectrum. A photodetection system, which includes a CCD camera operating in the infra-red spectrum (e.g., an infra-red CCD camera) with a fish-eye lens, may be located in the top of the cylinder as part of the laser and may capture cylinder images 320 using the light energy reflected off the interior of the cylinder. The captured images may include images of the cylinder walls 215, cylinder-facing surface of intake and exhaust valves 52 and 54, piston top surface 213 and the interior of cylinder 30. The captured images 220 are transmitted wirelessly by photodetector 94 to controller 12 for viewing on display 135 in a vehicle's center-console 140.

Center-console 140 may be included on a vehicle dashboard inside a vehicle cabin of the hybrid propulsion system 10 of FIG. 1. Center-console 140 may be a control-bearing surface located in a central part of the vehicle cabin, in particular, in the front of the vehicle cabin. Center-console 140 may include various controls, such as knobs 138, dials 142, and buttons 136. The various controls may be actuated by a vehicle operator to adjust cabin conditions. The various controls may include, for example, a volume control knob 138 coupled to a music system of the vehicle for adjusting a volume of music in the cabin, a tuning button 136 coupled to a radio system of the vehicle for adjusting radio channel selection, and a temperature controlling dial 142 coupled to the vehicle's HVAC system for adjusting cabin heating and cooling temperatures.

The center-console 140 may also include a display 135. The display may be a touch-sensitive display that enables the vehicle operator to select settings of the vehicle via touch interactions. The display may also be used to display current vehicle settings. In addition, the display may be used to display a navigation system, such as GPS, phone capabilities, or web applications to be accessed during travel. During conditions when the laser ignition device is operated in to capture images for diagnostic purposes, display 135 is used to depict images of the inside of cylinder 30 which are taken by photodetector 94 coupled to a laser detection system 92. Specifically, images of the interior of the cylinder taken by a CCD camera of the laser detection system are transmitted, for example wirelessly, to the engine control system and displayed on display 135 to a vehicle operator (e.g., a mechanic). Based on an operator display preference selected via touch interactions on the display, images of the cylinder interior of any or all the cylinders may be displayed.

In some examples, during the diagnostic mode, one or more of knobs 138 may be activated for engine position control (and deactivated for cabin control). For example, when operating in a diagnostic mode, the volume control knob may be activated for engine position control and deactivated for volume control. Consequently, adjustments to the volume control knob 138 can be used to adjust the engine position from an initial engine position to assist in the visual inspection of the cylinder. For example, it may be determined that the piston of the cylinder is positioned at or near a top of the cylinder currently displayed on display 135, obstructing a full view of the interior of the cylinder. To improve the view, the vehicle operator may slowly turn the volume control knob (e.g., clockwise or counterclockwise) which in turn moves the engine position (e.g., backwards or forwards) such that the piston is slowly moved towards the bottom of the cylinder via adjustments to a power-split generator/motor of the engine system. In embodiments where the engine includes a planetary gear transmission, the motor may hold the outer ring still (which keep the tire wheels still), while the generator (or sun gear), rotates the engine using feedback from either a resolver of the generator position, or using the 60-2 crank wheel with hall-effect sensor position system for actual engine position feedback. This movement of the piston may allow the operator to receive images representing a more complete view of the interior of the cylinder, and enable him to make a more precise inspection. For example, the improved view may enable the operator to inspect the cylinder walls for scoring damage. Further, during the diagnostic mode, the same volume control knob, or an alternate center-console knob, dial, or button may be activated to enable the image of the cylinder displayed on display 135 to be magnified (e.g., zoomed in to or out of).

In one example, the low power light pulses may be emitted in the infra-red (IR) spectrum by the laser ignition device and the CCD camera may be configured to operate in the IR spectrum. In alternate embodiments, photodetector 94 may have a full-spectrum CCD camera that can be tuned to coordinate with the frequency of the laser; thus, the camera can operate in IR and other spectrums of light (e.g. daylight or light bulbs) and has the capability to disable the laser if non-IR light is detected. Upon observing the images, the vehicle operator (e.g., a service technician or mechanic) can actively make adjustments to a position of the piston in order to better view the cylinder. For example, during conditions where images 220 indicate that the piston is near a top of the cylinder (e.g., at TCD), additional adjustments allow for the engine to be tuned slowly and precisely in order to move the piston down to the bottom of the cylinder. In the depicted example, when the piston is near the top of the cylinder in view, the operator can adjust volume control knob 138 located on the vehicle's center-console 140, in order to turn the engine forward or backwards from an initial engine position. If the engine is turned backwards from the initial engine position to move the piston downwards, the controller may concurrently open an intake throttle of the engine to reduce expansion of the intake manifold.

FIGS. 3A-B show example operations of the laser system 92. LCU 90 causes laser exciter 88 to generate a low powered laser pulse shown at 302, which may be directed towards top surface 313 of piston 36. After emission, the light energy may be reflected off of the piston and detected by the photodetector 94. LCU 90 may receive operational instructions, such as a power mode, from controller 12. For example, during ignition, the laser pulse used may be pulsed quickly with high energy intensity to ignite the air/fuel mixture. Conversely, to determine the engine position, the controller may direct the laser system to sweep frequency at low energy intensity to determine piston position and identify one or more valve positions. For instance, frequency-modulating a laser with a repetitive linear frequency ramp may allow a determination of one or more piston positions in an engine. A detection sensor 94 may be located in the top of the cylinder as part of the laser system and may be calibrated to receive return pulse 304 reflected from top surface 313 of piston 36.

FIGS. 3A-B illustrate how laser system 92 may emit pulses in the direction of piston 36 in cylinder 30 described above with reference to FIG. 1. Pulses emitted by laser system 92, e.g., pulse 302 shown in FIG. 3A, may be directed toward a top surface 313 of piston 36. Pulse 302 may be reflected from the top surface of the piston and a return pulse, e.g., pulse 304, may be received by laser system 92, which may be used to determine a position of piston 36 within cylinder 30.

In some examples, the location of the piston may be determined by frequency modulation methods using frequency-modulated laser beams with a repetitive linear frequency ramp. Alternatively, phase shift methods may be used to determine the distance. By observing the Doppler shift or by comparing sample positions at two different times, piston position, velocity and engine speed information (RPM measurement) may be inferred. The positions of intake valve 352 and/or exhaust valve 354 may also be determined using a laser system. When cylinder identity (CID) is combined with piston location, the position of the engine may be determined and used to synchronize fuel delivery and valve timing. Such positional states of the engine may be based on piston positions and CIDs determined via lasers.

Controller 12 may further control LCU 90 and include non-transitory computer readable storage medium including code to adjust the location of laser energy delivery based on operating conditions, for example based on a position of the piston 36 relative to TDC. Controller 12 may also incorporate additional or alternative sensors for determining the operational mode of engine 20, including additional temperature sensors, pressure sensors, torque sensors as well as sensors that detect engine rotational speed, air amount and fuel injection quantity as described above with regard to FIG. 1. Additionally or alternatively, LCU 90 may directly communicate with various sensors, such as Hall effect sensors 118, whose inclusion is optional, for determining the operational or diagnostic mode of engine 20.

A laser system may also be utilized to measure cam position by, for instance, blocking emitted pulses during certain strokes of the engine cycle. For instance, in one embodiment, laser system 92 may be located near intake valve 352 so a measurement of piston position within the cylinder is prevented during the intake stroke of the drive cycle. During the intake stroke, valve 352 opens into the chamber and blocks emitted laser pulses from reflecting off of the top surface of the piston 313. For example, in FIG. 3B, because laser system 92 is placed in close proximity to intake valve 352, when cylinder 30 is in its intake stroke, valve 352 opens into the chamber and blocks the laser pulse, e.g. laser pulse 306, from reaching the top surface of the piston 313. Controller 12 may still be programmed to interpret the signal detected in order to determine the positions of the cams. For instance, in this example the controller may process a lack of signal received by sensor 94 to indicate that intake valve 352 is in the open position. This information and the geometry of the engine may be further processed by the controller to determine the position of the engine within its drive cycle. Although FIG. 3B exemplifies how an emitted pulse may be blocked by intake valve 352, other configurations are possible. For instance, the laser system may be located in close proximity to the exhaust valve instead of the intake valve. When placed in this location, pulses emitted may instead be blocked during the exhaust stroke of the drive cycle. A controller can be calibrated to account for such differences. As described in detail below, controller 12 can process data collected during the drive cycle to determine engine position.

The difference in time between emission of light pulse 302 and detection of the reflected light pulse 304 by photodetector 94 can be further compared to a time threshold as a means of determining whether degradation of the laser device has occurred. For example, in an internal combustion engine, the combustion chamber may be three to four inches in length. Based on this estimate, and the speed of light in a vacuum ($c=3.0\times10^8$ m/s), a pulse of light emitted by laser system 92 reflected from the top surface of piston 313 may be detected in the picosecond time range. A time threshold well beyond the expected picosecond time range (e.g. 1 nanosecond) may therefore be adopted as a reference to indicate degradation of the laser system. For example, a pulse emitted by laser system 92 whose detection by sensor 94 takes longer than 1 nanosecond may indicate a laser system out of alignment.

In some examples, engine system 20 may be included in a vehicle developed to perform an idle-stop when idle-stop conditions are met and automatically restart the engine when restart conditions are met. Such idle-stop systems may increase fuel savings, reduce exhaust emissions, noise, and the like. In such engines, engine operation may be terminated at a random position within the drive cycle. Upon commencing the process to reactivate the engine, a laser system may be used to determine the specific position of the engine. Based on this assessment, a laser system may make a determination as to which cylinder is to be fueled first in order to begin the engine reactivation process from rest. In vehicles configured to perform idle-stop operations, wherein engine stops and restarts are repeated multiple times during a drive operation, stopping the engine at a desired position may provide for more repeatable starts, and thus the laser system may be utilized to measure engine position during the shutdown (after deactivation of fuel injection, spark ignition, etc.) while the engine is spinning down to rest, so that motor torque or other drag torque may be variably applied to the engine, responsive to the measured piston/engine position, in order to control the engine stopping position to a desired stopping position. The piston position information of each cylinder can also be used to estimate crankshaft positions. As elaborated with reference to FIG. 10, based on the relative position of each cylinder's crankshaft, crankshaft degradation (such as due to a twisted or broken crankshaft) can be reliably identified. As shown therein, the interior of the spray pattern provides an indication of the illumination.

In another embodiment, when a vehicle shuts down its engine, either because the motor is turned off or because the vehicle decides to operate in electric mode, the cylinders of the engine may eventually stop in an uncontrolled way with respect to the location of the piston 36 in combustion cylinder 30 and the positions of intake valve 352 and exhaust valve 354. For an engine with four or more cylinders, there may always be a cylinder located between exhaust valve closing (EVC) and intake valve closing (IVC) when the crankshaft is at rest. FIG. 4 shows as an example an in-line four cylinder engine capable of directly injecting fuel into the chamber, stopped at a random position in its drive cycle, and how the laser ignition system may provide measurements that can be compared among the cylinders to identify engine position. It will be appreciated that the example engine position shown in FIG. 4 is exemplary in nature and that other engine positions are possible.

Inset in the figure at 413 is a schematic of an example in-line engine block 402. Within the block are four individual cylinders where cylinders 1-4 are labeled 404, 406, 408 and 410 respectively. Cross-sectional views of the cylinders are shown arranged according to their firing order in an example drive cycle shown at 415. In this example, the engine position is such that cylinder 404 is in the exhaust stroke of the drive cycle. Exhaust valve 412 is therefore in the open position and intake valve 414 is closed. Because cylinder 408 fires next in the cycle, it is in its power stroke and so both exhaust valve 416 and intake valve 418 are in the closed position. The piston in cylinder 408 is located near BDC. Cylinder 410 is in the compression stroke and so exhaust valve 420 and intake valve 422 are also both in the closed position. In this example, cylinder 406 fires last and so is in an intake stroke position. Accordingly, exhaust valve 424 is closed while intake valve 426 is open. The valve position information of each cylinder can also be used to estimate camshaft positions, as elaborated at FIG. 10.

Each individual cylinder in an engine may include a laser system coupled thereto as shown in FIG. 1 described above wherein laser system 92 is coupled to cylinder 30. These laser systems may be used for both ignition in the cylinder and determining cam and piston position within the cylinder as described herein. For example, FIG. 4 shows laser system 451 coupled to cylinder 404, laser system 453 coupled to cylinder 408, laser system 457 coupled to cylinder 410, and laser system 461 coupled to cylinder 406.

As described above, a laser system may be used to measure valve positions as well as the position of a piston within a cylinder chamber. For example, in the engine position shown in FIG. 3B, light from laser system 92 may be at least partially blocked from reaching the top of piston 313 in cylinder 30. Because the amount of light reflected is reduced compared to the amount of light reflected off of the top surface of the piston when emitted pulses are not blocked, controller 12 may be programmed to account for such differences and use the information to determine that intake valve 352 is open. Based on the order of valve operations within the drive cycle, controller 12 further determines that exhaust valve 354 is closed. Because the example given is based on a four cylinder engine, one of the cylinders will be in an intake stroke at all times. As such, the controller may be programmed to process data from all laser systems in order to identify a cylinder in its intake stroke. Based on this determination, and using the geometry of the engine, the position of the engine can be identified using the laser systems. Alternatively, as will be described in further detail below, a controller may also be programmed to process a series of measurements from a single laser detector coupled to a cylinder as a means of identifying the position of the engine.

The positions of the pistons in a cylinder may be measured relative to any suitable reference points and may use any suitable scaling factors. For example, the position of a cylinder may be measured relative to a TDC position of the cylinder and/or a BDC position of the cylinder. For example, FIG. 4 shows line 428 through cross-sections of the cylinders at the TDC position and line 430 through cross-sections of the cylinders in the BDC position. Although a plurality of reference points and scales may be possible during a determination of piston position, the examples shown here are based on the location of the piston within a chamber. For instance, a scale based on a measured offset compared to known positions within the chamber may be used. In other words, the distance of the top surface of a piston, shown at 432 in FIG. 4, relative to the TDC position shown at 428 and BDC position shown at 430 may be used to determine a relative position of a piston in the cylinder. For simplicity, a sample scale calibrated for the distance from the laser system to the piston is shown. On this scale, the origin 428 is represented as X (with X=0 corresponding to TDC) and the location 430 of the piston farthest from the laser system corresponding to the maximum linear distance traveled by the piston is represented as xmax (with X=xmax corresponding to BDC). For example, in FIG. 4, a distance 471 from TDC 428 (which may be taken as the origin) to top surface 432 of the piston in cylinder 404 may be substantially the same as a distance 432 from TDC 428 to top surface 432 of the piston in cylinder 410. The distances 471 and 432 may be less than (relative to TDC 428) the distances 473 and 477 from TDC 428 to the top surfaces of pistons in cylinders 408 and 406, respectively.

The pistons may operate cyclically and so their position within the chamber may be related through a single metric relative to TDC and/or BDC. Generally, this distance, 432 in the figure, may be represented as $\Delta X$. A laser system may measure this variable for each piston within its cylinder and then use the information to determine whether further action is to be performed. For instance, a laser system could send a signal to the controller indicating degradation of the crankshaft if the variable differs by a threshold amount among two or more cylinders. The variable X is understood to represent a plurality of metrics that may be measured by the system, one example of which is described above. The example given is based on the distance measured by the laser system, which may be used to identify the location of the piston within its cylinder.

With reference to FIG. 4, a controller can be programmed to determine the position of the engine using various methods. For example, the controller may be programmed to process a series of data collected from a single laser system, e.g. laser system 461 in cylinder 406, to determine the position each cylinder's piston, and thereby infer engine position. An example map of a laser system operating in two different low power modes to determine intake valve timing and piston position with respect to an engine position during an example engine cycle is shown in FIG. 5 and described below. Alternatively, the controller may be programmed to process data collected from two or more laser systems to determine the position of the engine.

FIG. 5 shows a graph 500 of example valve timing and piston position with respect to an engine position (crank angle degrees) within the four strokes (intake, compression, power and exhaust) of the engine cycle for a four cylinder engine with a firing order of 1-3-4-2. Graph 500 shows intake valve timing and piston position curves along with two example position determination modes of the laser system. A laser system, for example, laser system 461 coupled to cylinder 406 in FIG. 4, can emit a series of low-power pulses throughout the engine cycle, but detect two different light signals for valve position estimation and piston position estimation within a cylinder. With reference to the example shown in FIG. 4, laser system 461 may detect light energy reflected off of the top surface of the piston during the compression, power and exhaust strokes of the drive cycle when the intake valve is closed. This detection mode shown at 506 in FIG. 5 may be a first low power detection mode (referred to as LD1 in the depicted figure). While the laser detector senses light energy reflected from the top of the piston in LD1, it may not sense the position of intake valve 426 relative to exhaust valve 424. The controller may use the information generated during LD1 to determine the piston position of each cylinder. By then comparing the relative piston position between cylinders, crankshaft diagnostics may be performed.

Conversely, when the engine cylinder enters the intake stroke of the drive cycle, laser detector 461 may detect a reduced signal since its emission is at least partially blocked by the open intake valve. This detection mode shown at 508 may be a second low power detection mode (referred to as LD2 in the depicted figure). While in LD2, the laser detector may, for example, sense intake valve position but not the position of the piston within the cylinder chamber. The controller may use the information generated during LD2 to determine the intake valve position of each cylinder. By then comparing the relative intake valve position between cylinders, camshaft diagnostics may be performed. Further still, by comparing the crankshaft position and camshaft position of each cylinder, misalignments between the crankshaft and camshaft for each cylinder may be identified.

At 502, a valve lift profile is shown for intake valve 426. At the beginning of the intake stroke, the profile shows that the valve opens and then closes while the piston moves from TDC to BDC. Although a valve life profile is not shown for exhaust valve, e.g. exhaust valve 424, a similar profile may be optionally included to show the exhaust valve opens and then closes while the piston moves from BDC to TDC during the exhaust stroke of the engine drive cycle.

At 504, the cyclical nature of the piston is shown for the four strokes of the drive cycle. For example, a piston gradually moves downward from TDC, bottoming out at BDC by the end of the intake stroke. The piston then returns to the top, at TDC, by the end of the compression stroke. The piston then again moves back down, towards BDC, during the power stroke, returning to its original top position at TDC by the end of the exhaust stroke. As depicted, the map illustrates an engine position along the x-axis in crank angle degrees (CAD). For the example curve given, a piston position is not shown during the intake stroke to illustrate the signal being reduced due to substantially blocked laser pulses (e.g. more than 90% blocked).

Sample data sets are shown at 510 and 512 to illustrate how different data sets may be collected by the laser system. For example, laser system 461 may begin collecting data following an engine shutdown command as the engine completes its last few cycles before coming to rest at position P1. Because P1 is located in an intake stroke, 510 shows that the signal collected by the laser detector may be disrupted by the intake valve. As the valve opens, the pulse emitted is at least partially blocked, which may result in a substantially reduced signal. Controller 12 may process this signal to identify the open intake valve and use a laser system coupled to another cylinder, e.g. laser system 457 coupled to cylinder 410, to measure its piston position. The geometry of the engine may then be used to relate all of the variables as a means of identifying the crankshaft or camshaft position.

Because the action of the drive cycle is cyclical in nature, during certain parts of the drive cycle, a second set of data may be collected whose initial curve shape may be substantially identical to that shown in 510. To distinguish these two regions from each other and uniquely identify the position of the engine, the controller may be programmed to process a series of data to determine engine position from curve shape. At 512 a second curve is shown as the piston in cylinder 406 approaches TDC during the compression stroke of the drive cycle. However, because the intake valve remains closed during both the compression and power strokes, no blockage of the laser signal occurs and a smooth set of data is detected. The controller may be programmed to process such data, and use the shape of the curve along with the geometry of the engine, to identify the position of the engine, as well as cylinder crankshafts and camshafts.

Figure 6:
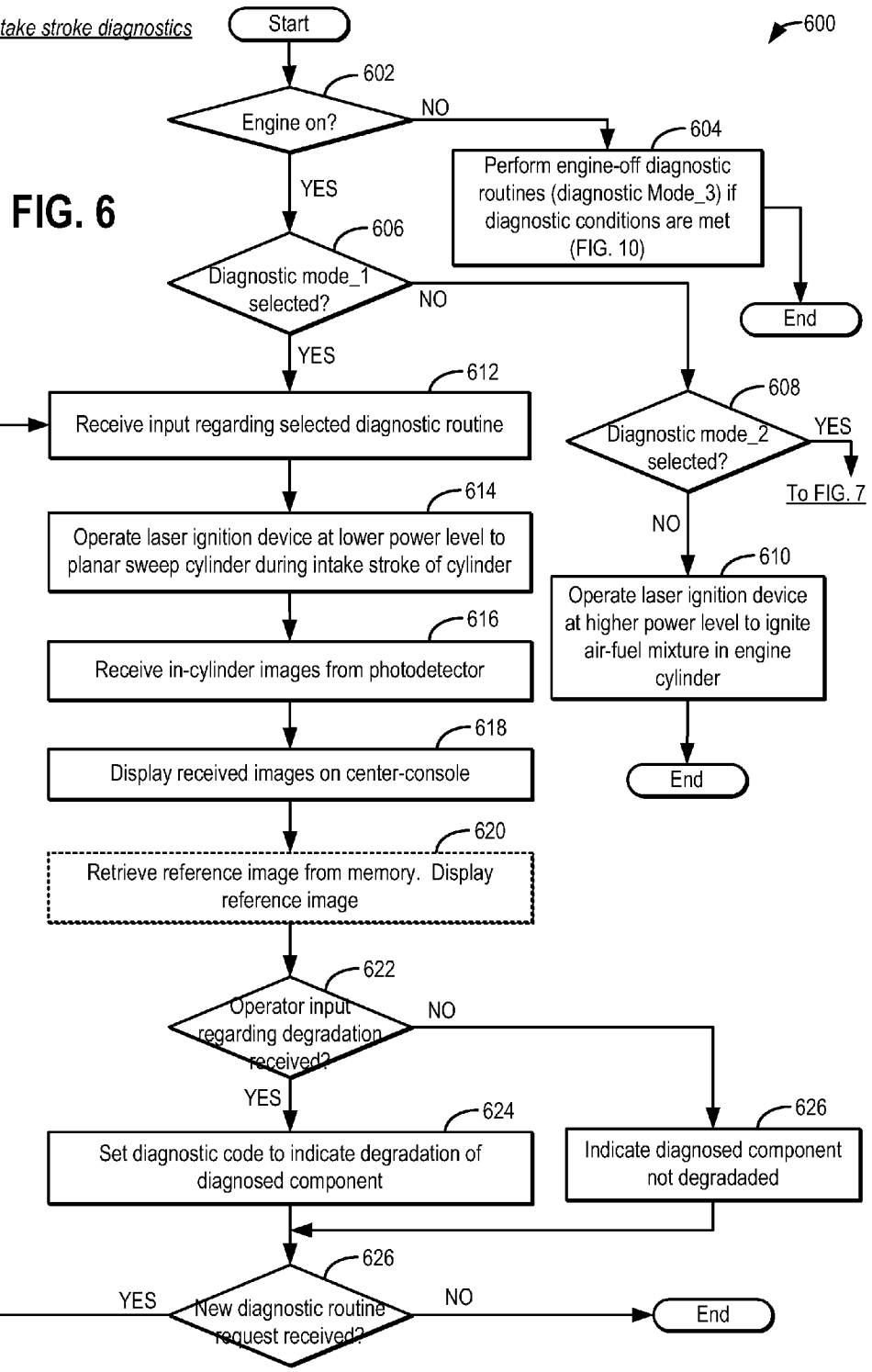
FIG. 6 shows a high level flow chart of a method for diagnosing degradation of one or more cylinder components based on in-cylinder images generated by a photodetector during an intake stroke.

Now turning to FIG. 6, an example method 600 is shown for performing a diagnostic routine to diagnose various in-cylinder components using light from a low power laser pulse emitted by an engine laser ignition system, such as the laser system of FIG. 1. The diagnostic mode depicted at FIG. 6 allows for the detection of various components during an intake stroke of a cylinder's combustion cycle.

At 602, it may be confirmed that the engine is on and operating. For example, it may be confirmed that the hybrid propulsion system is in an engine mode of operation. If not, the routine moves to 604 to perform engine-off diagnostic routines if diagnostic conditions have been considered met. If the engine is on, then at 606, it is determined if a first diagnostic mode (Mode_1) has been selected. The first diagnostic mode may be selected if specified operating conditions are met. For example, engine combusting conditions may be confirmed. Alternatively, a threshold duration or distance may have elapsed since a last iteration of the first diagnostic mode. When operating in the first diagnostic mode, laser pulses may be emitted in a lower power range during an intake stroke of each cylinder. As such, a plurality of diagnostic routines, each directed to one or more cylinder components, may be performed while operating in the first diagnostic mode.

If the first diagnostic mode is not selected, the routine moves to 608 to determine if a second diagnostic mode (Mode_2) has been selected. The second diagnostic mode may be selected if specified operating conditions are met. For example, engine combusting conditions may be confirmed. Alternatively, a threshold duration or distance may have elapsed since a last iteration of the second diagnostic mode. As such, a plurality of diagnostic routines, each directed to one or more cylinder components, may be performed while operating in the first diagnostic mode. If second diagnostic mode conditions are confirmed, the routine moves to FIG. 7 to perform diagnostic routines in the second mode. When operating in the second diagnostic mode, laser pulses may be emitted in a higher power range during a compression stroke of each cylinder. If neither the first nor the second diagnostic mode is confirmed, the routine moves to 610 where the laser ignition device is operated at a higher power level (above a threshold power level) so as to ignite an air-fuel mixture in the engine cylinder. Therein, the laser ignition device is operated during a compression stroke of the cylinder at the higher power to initiate fuel combustion in the cylinder.

Returning to 606, if the first diagnostic mode is confirmed, then at 612, the routine includes receiving input regarding a selected diagnostic routine. As discussed above, various diagnostic routines directed to various cylinder components may be performed while operating in the first diagnostic mode. The controller may receive input from a vehicle operator, such as via display 135 of FIG. 2, regarding the component to be diagnosed in the first operating mode. The in-cylinder components or conditions diagnosed while operating in the first diagnostic mode may include, as non-limiting examples, a cylinder fuel injector (e.g., to diagnose the injector's spray pattern), cylinder piston ring (e.g., to diagnose for leakage past the rings), cylinder carbon build-up, poor intake airflow, and the presence of a foreign object in the cylinder. As such, based on the component to be diagnosed, the number, location, and angle of images captured by a photodetector of the laser system, as well as a reference image displayed, may vary.

At 614, after receiving the input, the routine includes operating a laser ignition device (e.g., the laser system of FIG. 1) during an intake stroke of a cylinder at lower power. Operating at lower power includes operating at a power lower than a threshold power required for initiating cylinder combustion. By operating the laser ignition device at the lower power during the intake stroke, laser pulses may be directed into the cylinder to planar sweep the cylinder during the intake stroke. By virtue of the laser rapidly sweeping the interior of the cylinder during the intake stroke, the cylinder may be illuminated, as if by a light bulb, and the illumination may be used to capture images of the interior of the cylinder, thereby allowing an operator to observe and assess the interior of the cylinder without necessitating removal of the components for visual inspection.

In some examples, the planar sweep may be based on the cylinder component or condition being diagnosed. For example, when diagnosing a spray pattern of a fuel injector, the planar sweep of the laser ignition device may be oriented into a spray path of the cylinder fuel injector. The laser may be swept in a plane into the path of the injector spray at precise times after the beginning of the fuel injection during the intake stroke. In comparison, when diagnosing a cylinder piston ring, the planar sweep may be oriented towards the piston surface. The planar sweep used during fuel injector analysis may be a broader sweep than the sweep used for piston analysis. As elaborated below, the determination of component degradation may be based on input from the operator or may be an automated determination.

In some embodiments, since the engine is coupled in a hybrid electric vehicle, the routine may include maintaining a reference engine speed and load during the operating of the laser ignition device via adjustments to an electric motor. This allows the engine speed and load to be precisely controlled to a predetermined condition for each diagnostic test, improving the accuracy and reliability of the results. It also reduces variability in test results due to changes in engine conditions.

At 616, the routine includes receiving in-cylinder images from the photodetector. Specifically, the photodetector may use the light energy from the laser pulse emission to capture images of the interior of the cylinder. The captured images are then transmitted to the display device, for example, wirelessly. In some examples, photodetector camera settings applied during the different diagnostic routines of diagnostic mode_1 may vary based on the component being diagnosed. The camera settings adjusted may include, for example, shutter opening duration, aperture settings, time of image capture, etc. As an example, during fuel injector analysis, the camera shutter may be opened for a longer duration so that several sweeps of the cylinder are captured in a single image. In comparison, during cylinder wall carbon build-up analysis, the camera shutter may be opened for a shorter duration and multiple images may be captured over the several sweeps.

At 618, the routine includes displaying the in-cylinder image(s), captured by the photodetector, to a vehicle operator on the display device. Herein, the vehicle operator may be, for example, a mechanic or service technician diagnosing the engine. For example, after each planar sweep of the laser, the captured image may be automatically presented to the service technician for analysis.

Optionally, at 620, the controller may display a reference image of the component or condition being diagnosed to the vehicle operator on the display device. The reference image may be stored in, and retrieved from, the controller's memory. Furthermore, the reference image may be a reference image previously generated by the photodetector, such as during predetermined conditions (e.g., on a previous iteration of the given diagnostic routine when no degradation was detected). The reference image may be retrieved based on the input regarding the diagnostic routine previously received at 612. Additionally, the reference image may be selected based on the generated image. Alternatively, the reference image may be retrieved and displayed following operator input received via the display device after display of the captured image(s) on the display device. As an example, when the cylinder component being diagnosed is a cylinder fuel injector, such as a cylinder port fuel injector, the in-cylinder image generated by the photodetector may be indicative of a spray pattern of the fuel injector, such as a spray pattern of the port fuel injector. The reference image retrieved by the controller may be of an expected spray pattern from a properly functioning fuel injector. An example of such a comparison is discussed herein with reference to FIG. 10. Based on differences between the expected pattern and the actual pattern, the operator may be able to indicate fuel injector degradation. Specifically, the comparison of two images may provide objective evidence of the need for replacement of the fuel injector.

At 622, the routine includes receiving input from the vehicle operator regarding a health of the component or condition being diagnosed, the operator input based on the displayed in-cylinder image and reference image. For example, the operator may compare the displayed image with the reference image, and based on a large discrepancy, the operator may indicate that component degradation has occurred.

In one example, the cylinder component being diagnosed may be the cylinder piston rings and the in-cylinder image generated may be indicative of a state of the cylinder piston rings. The reference image displayed may include an image of the cylinder piston during an intake stroke. If the in-cylinder image captured by the photodetector during the intake stroke is indicative of crankcase vapor condensation at the piston, the operator may indicate that the cylinder piston rings are degraded and vapors coming from the crankcase are condensing in the cylinder near the piston.

As another example, the cylinder component being diagnosed may be a cylinder combustion chamber and the in-cylinder image may be compared to a reference image to indicate if a foreign object is present (e.g., bounding around) in the combustion chamber. For detecting the presence of foreign objects, still and/or video images captured by the photodetector may be used. The still images may include time lapsed still images captures over an intake stroke and an exhaust stroke (such as the exhaust stroke immediately preceding the intake stroke). If video images are analyzed, the analysis may include the playback of video images captured during the intake stroke and the exhaust stroke. The video images may be played back in slow motion to detect foreign objects (such as a nut, bolt, rag, etc.) that may be bouncing around in the cylinder. The foreign object may have entered the cylinder during prior maintenance operations or engine assembly, such as when the air intake was assembled. In response to the detection of a foreign object, a diagnostic code may be set to indicate that the object needs to be removed from the specific cylinder.

As still another example, the images of the interior of the cylinder captured during the intake stroke may be analyzed to assess carbon build-up in the cylinder. Therein, the image of the cylinder wall may be studied and the reflectivity of the wall may be noted. The reflectivity of the cylinder wall in the captured image may be compared to the reflectivity of the cylinder wall in a reference image of a clean cylinder. As such, a clean cylinder may generate a shiny image with a high reflectivity of the cylinder wall. In comparison, a cylinder with soot build-up may generate a dull or black image with a low reflectivity of the cylinder wall. Thus, based on the images indicating a drop in cylinder wall reflectivity, it may be determined that there is excessive carbon or soot build-up on the cylinder wall. In response to the build-up, a diagnostic code may be set to indicate soot build-up. The controller may also direct the engine to run leaner than stoichiometry for a period of time or direct the laser to burn-off areas with excessive carbon build-up to address the elevated cylinder soot levels. The controller may also direct the diagnostic to investigate the piston ring integrity by scrutinizing the images from that test.

As such, analysis of images captured during an intake stroke for cylinder wall carbon build-up analysis may be different from analysis of images captured during an exhaust stroke for misfire detection. Therein, high reflectivity of the cylinder wall during the exhaust stroke may be indicative of a hot spot which can increase the propensity for misfires. Therefore, in response to high cylinder wall reflectivity observed during an exhaust stroke, a hot spot with carbon build-up may be determined and soot burn off may be requested. In comparison, in response to low cylinder wall reflectivity observed during an intake stroke, carbon build-up may be determined and soot burn off may be requested.

Figure 11:
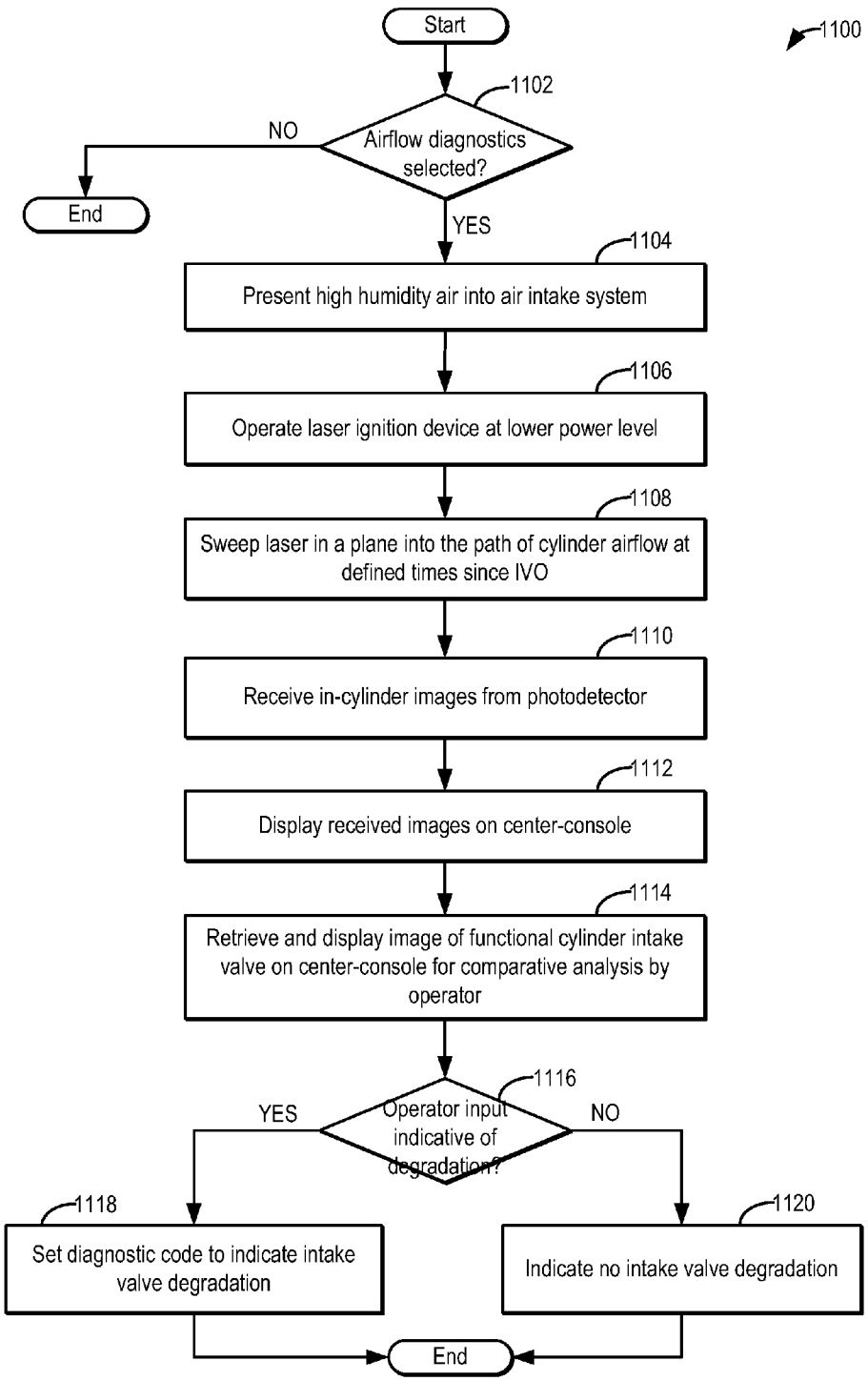
FIGS. 11-13 show example routines for diagnosing degradation of various engine components, according to the present disclosure.

In yet another example, elaborated herein with reference to FIG. 11, the cylinder component diagnosed may be an intake valve, wherein the in-cylinder image captured at different times since intake valve opening may be compared to a reference image to indicate coolant entry or leakage into the cylinder via the intake valve.

If operator input indicative of degradation is received, then at 624, in response to the operator input, the routine includes setting a diagnostic code to indicate component degradation. The diagnostic code may also indicate component replacement or repair is required, as appropriate. If component degradation is not determined by the operator, then at 626, the routine indicates that the diagnosed component or condition is not degraded and that the component is in good health.

From 624 and 626, the routine moves to 628 wherein it is determined if a new diagnostic routine request has been received. For example, it may be determined if conditions for another diagnostic routine that uses illumination from low power laser operation in the intake stroke have been met. If yes, the routine returns to 612 to receive input regarding the diagnostic to be performed and the component or condition to be diagnosed. The routine is then reiterated. The routine of FIG. 6 is reiterated from 612 to 628 to complete all the diagnostic routines that can be performed while operating in the first diagnostic mode. If conditions for a particular diagnostic routine are not met, or if a sufficient number (e.g., all) of the diagnostic routines of Diagnostic mode_1 are completed, routine 600 may end.

While the above routine depicts the need for an operator to analyze the generated image(s) and indicate whether component degradation has occurred, in alternate embodiments, the analysis may be automated. For example, following image capture in the intake stroke, the image may be automatically displayed on the display device, and a corresponding reference image may also be automatically displayed on the display device. The controller may then compare the images, without requiring operator input, to provide a pass/fail result of the diagnostic routine. The pass/fail determination may be based on similarity of the images (that is, the generated image and the reference image) via a simpler, less computation-intensive pixel comparison or an advanced, more computation-intensive image analysis. In the advanced image analysis, objects within the image may be identified for a more precise evaluation of the component or condition being studied.

It will be further appreciated that while the above routine suggests the use of the laser system coupled to the engine for diagnostic purposes, in alternate examples, the laser system including the laser exciter, the lenses, and the photodetector, may be configured as a mobile laboratory tool. Therein, the laser system may be configured as a portable tool that can be coupled to any engine, such as an engine with spark plugs, or an engine that has been removed from a vehicle, and used for analyzing the engine. As an example, the mobile tool may be placed in the intake manifold, or intake port, of an engine, to view and analyze the injector spray pattern (such as the port injector spray pattern) for the engine. As another example, in the case of engines with spark plugs, the mobile tool may be advantageously used for analyzing spark quality as well as spark plug fouling. As a further example, a cylinder spark plug may be removed and the mobile tool may be placed in the position of the spark plug for capturing images of an interior of the cylinder and analyzing other in-cylinder components. As such, the mobile tool may provide various advantages over spark-plug based tools. For example, by replacing the spark plug with a laser, spark plug fouling may not be induced with prolonged use, as may occur in a laboratory setting. As another example, the mobile tool may include its own video display unit and processing for use on vehicles that do not possess the laser diagnostic interface display.

In one example, a hybrid vehicle system comprises an engine includes a cylinder; an electric motor; a display device in a cabin of the vehicle; as well as a laser ignition system coupled to a cylinder head and configured to direct light pulses into the cylinder. The engine further includes a photodetection system coupled to the laser ignition system and the cylinder for generating images of an inside of the cylinder using the light pulses from the laser ignition system. The photodetection system may include, for example, a CCD camera with a fish-eye lens. The vehicle system may further include a controller with non-transitory memory and computer readable instructions for: operating the laser ignition system during the intake stroke at a lower power level; displaying an in-cylinder image generated at the photodetection system following the operating to a vehicle operator on the display device; and further displaying a reference image retrieved from the controller's memory on the display device, the reference image based on the generated in-cylinder image. The controller may receive input from the vehicle operator via the display device indicative of cylinder component degradation and set a diagnostic code based on the received input. The controller may include further instructions for adjusting an output of the electric motor when operating the laser ignition system to maintain a reference engine speed and load while generating the in-cylinder image. The reference engine speed and load may correspond to predetermined conditions for the specific diagnostic routines. This allows for better control over the operating conditions under which the images are captured in relation to those when the reference image was captured.

Figure 7:
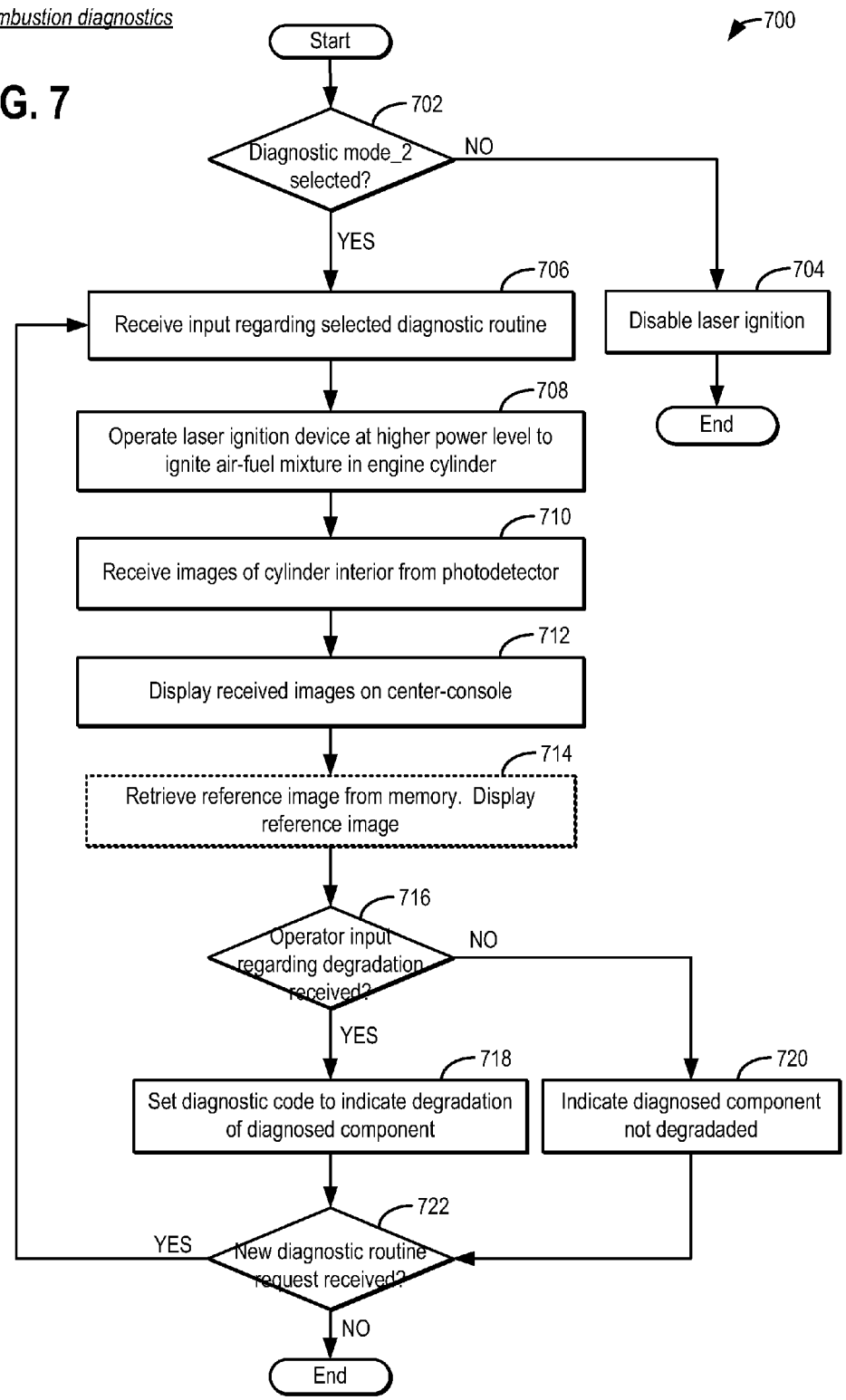
FIG. 7 shows a high level flow chart of a method for diagnosing degradation of one or more cylinder components based on in-cylinder images generated by a photodetector using light from a cylinder combustion event.

Now turning to FIG. 7, an example method 700 is shown for performing a diagnostic routine to diagnose various in-cylinder components using light from a high power laser pulse emitted by an engine laser ignition system, such as the laser system of FIG. 1. The diagnostic mode depicted at FIG. 7 allows for the detection of various components during a cylinder combustion event.

At 702, it is determined if a second diagnostic mode (Mode_2) has been selected. The second diagnostic mode may be selected if specified operating conditions are met. For example, engine combusting conditions may be confirmed. Alternatively, a threshold duration or distance may have elapsed since a last iteration of the second diagnostic mode. As such, a plurality of diagnostic routines, each directed to one or more cylinder components, may be performed while operating in the second diagnostic mode.

If the first diagnostic mode is not selected, the routine moves to 608 to determine if a second diagnostic mode (Mode_2) has been selected. The second diagnostic mode may be selected if specified operating conditions are met. For example, engine combusting conditions may be confirmed. Alternatively, a threshold duration or distance may have elapsed since a last iteration of the second diagnostic mode. As such, a plurality of diagnostic routines, each directed to one or more cylinder components, may be performed while operating in the first diagnostic mode. If second diagnostic mode conditions are not confirmed, at 704, laser ignition may be disabled. Laser ignition may then remain disabled until cylinder ignition is required, or until conditions for a diagnostic routine of Mode_2 are confirmed.

If the second diagnostic mode is confirmed, at 706, the routine includes receiving input regarding a selected diagnostic routine. As discussed above, various diagnostic routines directed to various cylinder components may be performed while operating in the second diagnostic mode. The controller may receive input from a vehicle operator, such as via display 135 of FIG. 2, regarding the component to be diagnosed in the second operating mode. The in-cylinder components or conditions diagnosed while operating in the second diagnostic mode may include, as non-limiting examples, the conditions of a cylinder piston head, alignment of a converging lens of the laser system, cylinder combustion parameters such as flame propagation, flame initiation, as well as air-fuel ratio control. As such, based on the component or conditions to be diagnosed, the number, location, and angle of images captured by a photodetector of the laser system, as well as a reference image displayed, may vary.

At 708, after receiving the input, the routine includes initiating cylinder combustion by operating a laser ignition device (e.g., the laser system of FIG. 1). This may include operating the laser ignition device at a higher power level, such as at a power level higher than a threshold power required for only illuminating an interior of the cylinder. In addition, the laser ignition device may be operated to direct laser pulses into the cylinder to planar sweep the cylinder during a compression stroke of the cylinder. For example, the laser pulses may be directed at the center of the cylinder to give a smooth, even, and completion combustion pattern with the entire cylinder starting from a point or line in the center and moving radially outwards to the walls, ending at the same instant. In addition, crevice spaces may get an additional hit. In this way, the light from the ignition flame may be used for combustion flame analysis. By virtue of the laser rapidly sweeping the interior of the cylinder during the compression stroke, cylinder combustion may be initiated and the cylinder may be illuminated, as if by a light bulb, using the light generated from cylinder combustion. The illumination may be used to capture images of the interior of the cylinder, thereby allowing an operator to observe and assess the interior of the cylinder without necessitating removal of the components for visual inspection. In some examples, as discussed previously, the planar sweep may be based on the cylinder component or condition being diagnosed. As such, since the flame may obscure the view of the cylinder parts during the combustion, the light bulb effect is provided only with low energy laser sweeping when the flame is complete In some embodiments, where the engine is coupled in a hybrid electric vehicle, the routine may include maintaining a reference engine speed and load during the operating of the laser ignition device via adjustments to an electric motor. This allows the engine speed and load to be precisely controlled to a predetermined condition for each diagnostic test, improving the accuracy and reliability of the results. It also reduces variability in test results due to changes in engine conditions.

At 710, the routine includes receiving in-cylinder images from the photodetector. Specifically, the photodetector may use the light generated from the cylinder combustion (following laser ignition) to capture images of the interior of the cylinder. The captured images are then transmitted to the display device, for example, wirelessly.

At 712, the routine includes displaying the in-cylinder image(s), captured by the photodetector, to a vehicle operator on a vehicle display device. Herein, the vehicle operator may be, for example, a mechanic or service technician diagnosing the engine. For example, after each combustion event, the captured image may be automatically presented to the service technician for analysis. Alternatively, after every combustion event, an image of each laser sweep may be sent to the operator.

Optionally, at 714, the controller may display a reference image of the component or condition being diagnosed to the vehicle operator on the display device. The reference image may be stored in, and retrieved from, the controller's memory. The reference image may include a reference image previously generated by the photodetector during predetermined conditions, such as on a previous iteration of the given diagnostic routine when no degradation was detected. The reference image may be retrieved based on the input regarding the diagnostic routine previously received at 706. Additionally, the reference image may be selected based on the generated image. Alternatively, the reference image may be retrieved and displayed following operator input received via the display device after display of the captured image(s) on the display device.

As an example, when the cylinder component being diagnosed is a piston, the in-cylinder image generated by the photodetector may be indicative of a piston head. The reference image retrieved by the controller may be of a functional (that is, undegraded) piston head of similar age. Based on differences between the reference image and the actual image, the operator may be able to indicate piston head degradation, such as piston head melting. Specifically, the comparison of the two images may provide objective evidence of the need for replacement of the piston.

At 716, the routine includes receiving input from the vehicle operator regarding a health of the component or condition being diagnosed, the operator input based on the displayed in-cylinder image and reference image. For example, the operator may compare the displayed image to the reference image, and based on a discrepancy, the operator may indicate that component degradation has occurred.

In one example, the cylinder combustion parameter being diagnosed may be cylinder combustion flame propagation. The captured image displayed may include time lapsed images of the flame front, including images of flame progression from the center of the cylinder outwards. The images may be captures at precise times including and following the laser ignition event. The reference image displayed may likewise include time lapsed images of the flame front, as expected, from the center of the cylinder outwards at the corresponding times in a good known cylinder. If the shape and/or intensity of the flame as it progresses in the captured image does not match the expected shape and intensity, as shown in the reference image, degradation of flame propagation may be determined. For example, the flame front in the reference image may form a ball-like shape. If the captured image does not show a flame front with a ball-like shape, improper flame propagation may be determined. As another example, if the flame front in the captured image has a lower intensity than the flame front of the reference image, improper flame propagation may be determined. In response to the indication of flame front degradation, a diagnostic code may be set. If the remaining laser diagnostics all pass (that is, no degradation is determined), further analysis of the fuel or compression is required may be indicated. Otherwise, the degraded cylinder component or laser control system is identified by the remaining diagnostics with a unique diagnostic code.

As another example, the combustion parameter diagnosed may include flame initiation. This reflects the location where the flame front originates. For example, the generated images may be indicative of a location on the piston head where the flame front initiated. Since the combustion is initiated via laser ignition, the location of flame front initiation correlates with the location of lens convergences produces laser intensity sufficient to cause combustion in the mixture, or where the laser may impinge in the cylinder. That is, the captured image is indicative of an orientation of laser pulses output by the laser ignition device. The reference image may indicate a location on the piston head where the flame front is expected to initiate and the laser is expected to hit first. If the captured image indicates that the location of flame initiation is askew relative to the expected location (e.g., makes a chord), degradation may be indicated. Specifically, incorrect orientation or aiming of the laser may be indicated. In response to the indication of incorrect orientation, a diagnostic code may be set to fix the alignment of the laser device.

The generated images of a location on the piston head where the flame front initiated may also be indicative of a focal point of a lens (such as a converging lens) coupled to the laser ignition device. Since the location of flame front initiation correlates with the location where the intensity of laser impingement is highest, assuming the alignment of the laser device is correct, the location of flame initiation correlates with the focal point of the converging lens. Furthermore, the location where the flame front intensity is the highest correlates with the focal point of the converging lens, which may be in the precise center of the cylinder volume or on the piston head. If the captured image indicates that the location of flame initiation is askew relative to the expected location (e.g., makes a chord), degradation may be indicated. Specifically, incorrect orientation of the lens and incorrect flame initiation may be indicated. Alternatively, the captured image may be used to calculate a distance from the laser where the spark occurred and flame initiated. If the calculated distance is different from the distance calculated based on the reference image, incorrect orientation of the lens may be determined. In response to the indication of incorrect orientation of the lens, a diagnostic code may be set to fix the alignment of the lens.

It will be appreciated that in some examples, analysis of the location of flame initiation may require a specific orientation of the photodetector camera relative to the laser. For example, the photodetector camera may be lateral to (e.g., on a side or edge of) the laser rather than aligned on top of the laser. As discussed below, this configuration may be achieved in mobile tool applications of the laser system.

As another example, the in-cylinder component being diagnosed may be a cylinder piston head. Therein, the scanned image of the piston head may be compared to a stored reference image of a similarly aged piston head without degradation. By comparing the images, a melted piston head may be detected and piston replacement may be objectively determined by the operator.

In yet another example, the spectral analysis may be used for combustion air-fuel ratio (AFR) control. Herein, the diagnostic routine may be performed as a part of various engine on-board diagnostic (OBD) routines. The spectral analysis may be used for AFR control independent of a UEGO sensor-based AFR control. Alternatively, the spectral analysis may be used to supplement or validate the UEGO based AFR control. Therein, the generated in-cylinder image(s) may be indicative of a location or timing of a stoichiometric point of combustion. As such, at any given time of engine operation, there may be at least one cylinder performing better (or worse) than all the others. Herein, the captured image may be used to indicate Lambda for each cylinder combustion event. The images may be captured and analyzed on every single combustion event or cylinder. Based on the captured image, cylinder specific precise air-fuel ratio control may be performed. The stoichiometric point for each cylinder may be learned and used to trim AFR errors. Specifically, air mass delivery and fuel injection timing may be fine-tuned for each cylinder. By enabling each cylinder to operate at Lambda more precisely, instead of operating too rich or too lean, overall engine fuel economy can be improved.

If operator input indicative of degradation is received, then at 718, in response to the operator input, the routine includes setting a diagnostic code to indicate component or condition degradation. The diagnostic code may also indicate component replacement or repair is required, as appropriate. If component degradation is not determined by the operator, then at 720, the routine indicates that the diagnosed component or condition is not degraded and that the component is in good health.

From 718 and 720, the routine moves to 722 wherein it is determined if a new diagnostic routine request has been received. For example, it may be determined if conditions for another diagnostic routine that uses illumination from high power laser operation during and following the ignition event have been met. If yes, the routine returns to 706 to receive input regarding the diagnostic to be performed and the component or condition to be diagnosed. The routine is then reiterated. The routine of FIG. 7 is reiterated from 706 to 722 to complete all the diagnostic routine that can be performed while operating in the second diagnostic mode. If conditions for a particular diagnostic routine are not met, or if a sufficient number (e.g., all) of the diagnostic routines of Diagnostic mode_2 are completed, routine 700 may end.

While the above routine depicts the need for an operator to analyze the generated image(s) and indicate whether component degradation has occurred, in alternate embodiments, the analysis may be automated. For example, following image capture, the image may be automatically displayed on the display device, and a corresponding reference image may also be automatically displayed on the display device. The controller may then automatically compare the images, without requiring operator input, to provide a pass/fail result of the diagnostic routine. The pass/fail determination may be based on similarity of the images (that is, the generated image and the reference image) via a simpler, less computation intensive pixel comparison or an advanced, more computation intensive image analysis. In the advanced image analysis, objects within the image may be identified for a more precise evaluation of the component or condition being studied.

It will be further appreciated that while the above routine suggests the use of the laser system coupled to the engine for diagnostic purposes, in alternate examples, the laser system including the laser exciter, the lenses, and the photodetector, may be configured as a mobile laboratory tool. Therein, the laser system may be configured as a portable tool that can be coupled to any engine, such as an engine with spark plugs, or an engine that has been removed from a vehicle, and used for analyzing the engine. As an example, the mobile tool may be placed in the intake manifold, or intake port, of an engine, to view and analyze flame front initiation. This may include separating the laser system components and localizing the laser and the photodetector at different locations of the intake port for a given diagnostic routine.

In this way, a method is provided for visual inspection of engine components without requiring engine teardown. The method comprises operating a laser ignition device during a compression stroke to initiate cylinder combustion; transmitting an in-cylinder image generated after operating the laser ignition device to a vehicle display device, the image generated by a photodetector of the cylinder using light generated via the cylinder combustion; and based on input received from an operator, setting a diagnostic code indicating degradation. Herein, the photodetector is coupled to the cylinder, the photodetector including a lens and a camera. The in-cylinder image captured is an image of a cylinder component or combustion parameter. The method further comprises displaying a reference image to the operator on the vehicle display device, the reference image selected based the cylinder component or combustion parameter. Indicating degradation includes indicating degradation of the cylinder component or combustion parameter being diagnosed. For example, when the in-cylinder image is an image of combustion flame initiation, indicating degradation includes indicating degradation of the photodetector lens.

In one example, a hybrid vehicle system comprises an engine includes a cylinder; an electric motor; a display device in a cabin of the vehicle; a laser ignition system coupled to a cylinder head and configured to direct light pulses into the cylinder; and a photodetection system coupled to the laser ignition system and the cylinder for generating images of an inside of the cylinder using the light pulses from the laser ignition system. The vehicle system may include a controller with non-transitory memory and computer readable instructions for operating the laser ignition system during the compression stroke to initiate cylinder combustion; displaying an in-cylinder image generated at the photodetection system following the operating to a vehicle operator on the display device; and further displaying a reference image retrieved from the controller's memory on the display device, the reference image based on the generated in-cylinder image. Operating the ignition device during the compression stroke may include operating the laser ignition system above a threshold power level. The photodetection system may then capture images of the interior of the cylinder during and following the ignition event using light generated by the cylinder combustion. The controller may then indicate cylinder combustion degradation based on operator input received following the displaying. As an example, the photodetection system may include a CCD camera with a fish-eye lens. Displaying the images may include wirelessly transmitting images within the vehicle system from the photodetection system to the display device. The controller may include further instructions for adjusting an output of the electric motor when operating the laser ignition system to maintain a defined engine speed and load while generating the in-cylinder image.

In this way, the routines of FIGS. 6-7 depict a method of using a laser ignition system at different power levels and at different times during a combustion cycle to diagnose various engine components. For example, a method for an engine is proved that comprises operating a laser ignition device during an intake stroke at a lower power level to generate a first in-cylinder image; operating the laser ignition device during a compression stroke at a higher power level to generate a second in-cylinder image; and displaying each of the first and second in-cylinder image to a vehicle operator on a display device. The method further includes receiving input from the vehicle operator indicative of degradation of a first cylinder component based on the first image, and input indicative of degradation of a second, different cylinder component based on the second image. For example, the first cylinder component may include one or more of a fuel injector, cylinder intake valve, and cylinder piston ring, while the second cylinder component may include one or more of a lens and laser of the laser ignition device.

Figure 8:
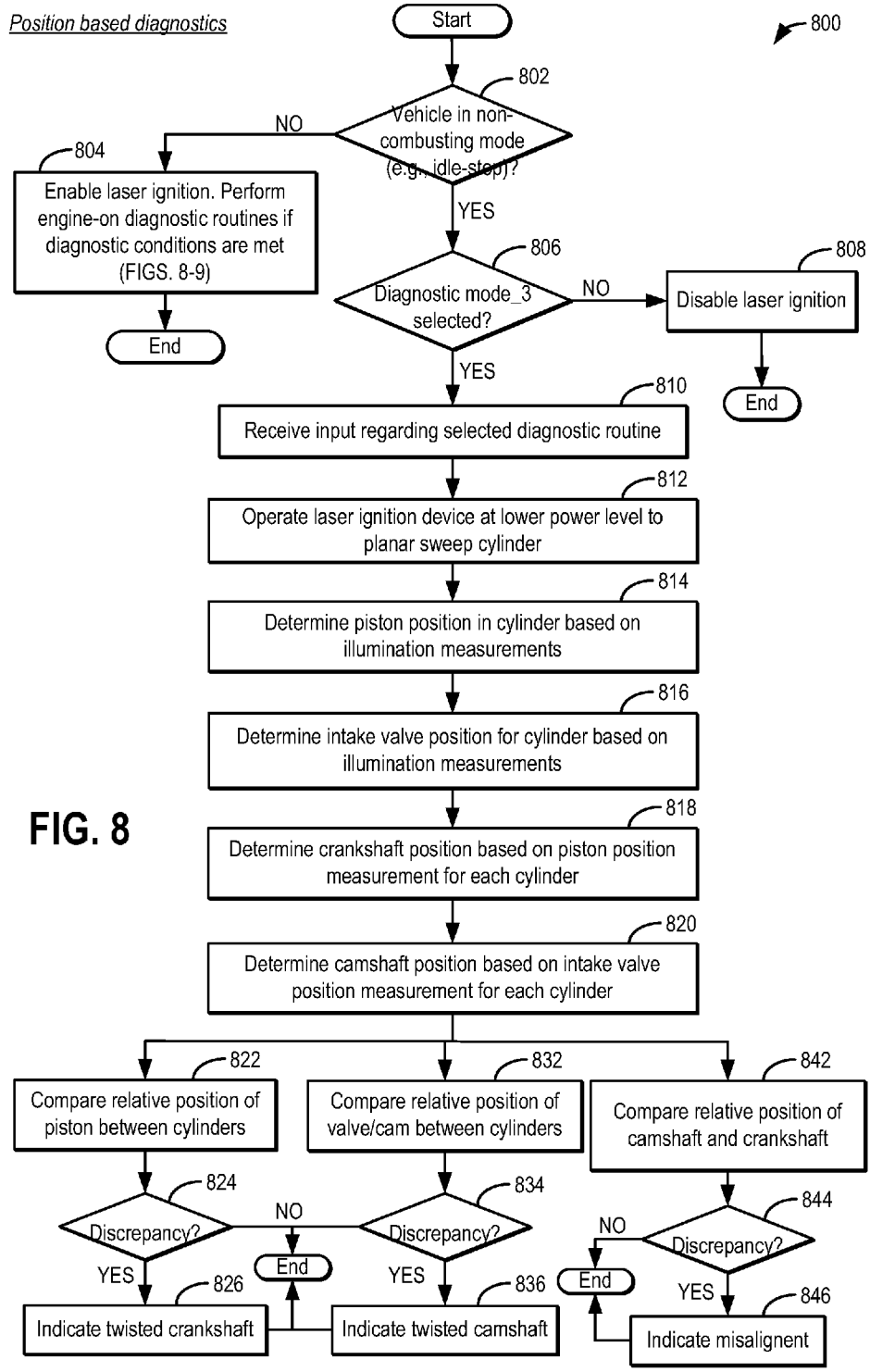
FIG. 8 shows a high level flow chart of a method for diagnosing degradation of one or more engine components based on piston position and intake valve position measurements performed using an engine laser ignition system.

Now turning to FIG. 8, an example method 800 is shown for performing a diagnostic routine to diagnose various in-cylinder components using illumination based position measurements following low power laser pulse emission by an engine laser ignition system, such as the laser system of FIG. 1. The diagnostic mode depicted at FIG. 8 allows for the diagnosis of various components based on their absolute or relative positions.

At 802, it may be confirmed that the engine is not combusting (e.g. engine-off). For example, it may be confirmed that the hybrid propulsion system is in an electric mode of operation or the engine is in an idle-stop mode. If not, the routine moves to 804 to perform engine-on diagnostic routines if diagnostic conditions have been considered met, such as the routines discussed at FIGS. 6-7. If the engine is not combusting, then at 806, it is determined if a third diagnostic mode (Mode_3) has been selected. The third diagnostic mode may be selected if specified operating conditions are met. For example, engine non-combusting conditions may be confirmed. Alternatively, a threshold duration or distance may have elapsed since a last iteration of the third diagnostic mode. When operating in the third diagnostic mode, laser pulses may be emitted in a lower power range into each non-combusting cylinder. As such, a plurality of diagnostic routines, each directed to one or more cylinder components, may be performed while operating in the third diagnostic mode.

If the third diagnostic mode is not selected, the routine moves to 808 to disable the laser ignition system. If the third diagnostic mode is confirmed, then at 810, the routine includes receiving input regarding a selected diagnostic routine. As discussed above, various diagnostic routines directed to various cylinder components may be performed while operating in the third diagnostic mode. The controller may receive input from a vehicle operator, such as via display 135 of FIG. 2, regarding the component to be diagnosed in the third operating mode. The in-cylinder components or conditions diagnosed while operating in the third diagnostic mode may include, as non-limiting examples, a cylinder crankshaft and a cylinder camshaft. In some examples, based on the component to be diagnosed, the number, frequency, orientation, and power level of the laser pulses emitted by the laser system may vary.

At 812, after receiving the input, the routine includes operating a laser ignition device in each cylinder. Specifically, a laser ignition device (e.g., the laser system of FIG. 1) may be operated during an intake stroke of a cylinder at lower power. Additionally or optionally, the laser ignition device may be operated during an exhaust stroke of each engine cylinder. Operating at lower power includes operating at a power lower than a threshold power required for initiating cylinder combustion. By operating the laser ignition device at the lower power during the intake stroke, laser pulses may be directed into the cylinder to planar sweep the cylinder during the intake stroke. By virtue of the laser rapidly sweeping the interior of the cylinder during the intake stroke, the cylinder may be illuminated, as if by a light bulb, and the illumination may be used to capture images of the interior of the cylinder, thereby allowing an operator to observe and assess the interior of the cylinder without necessitating removal of the components for visual inspection.

At 814, the routine includes identifying a piston position in each cylinder based on the operating of the laser ignition device. Identifying the piston position in each cylinder includes, for each cylinder, sensing light reflected off a top surface of the piston and estimating the piston position based on a time elapsed between the operating of the laser ignition device and the sensing of the light. For example, the location of the piston may be determined by frequency modulation methods using frequency-modulated laser beams with a repetitive linear frequency ramp.

At 816, the routine further includes identifying a cylinder valve position in each cylinder based on the operating of the laser ignition device. In one example, the cylinder valve is an intake valve. In other examples, the cylinder valve may be an exhaust valve. Identifying the cylinder valve position includes, for each cylinder, sending light reflected off the cylinder valve. As elaborated with reference to FIGS. 4-5, the laser system may be used to determine valve positions within a cylinder, in addition to the position of the piston. Therein, intake valve opening may be inferred in response to light from the laser system getting at least partially blocked from reaching the top of the cylinder piston. Because the amount of light reflected is reduced compared to the amount of light reflected off of the top surface of the piston when emitted pulses are not blocked, the controller may account for such differences and use the information to determine that the given cylinder's intake valve is open. Based on the order of valve operations within the drive cycle, the controller may also infer that the cylinder's exhaust valve is closed. In alternate examples, a drop in the amount of light reflected off the piston surface during laser operation during an exhaust stroke may be used to infer exhaust valve opening (and intake valve closing).

In embodiments where the intake valve and/or exhaust valve are coupled to respective cams, the illumination measurement data may also be used to infer the position of cams and camshaft(s) coupled to the valves. For example, for each cylinder, the controller may sense light reflected off the cylinder and estimate the cylinder's intake cam position based on a time elapsed between the operating of the laser ignition device and the sensing of the light.

At 818, the routine includes determining a crankshaft position for the engine based on the piston position measurement performed in each cylinder at 814. Likewise, at 820, the routine includes determining a camshaft position for the engine based on the cylinder valve (intake or exhaust valve) or cam (intake or exhaust cam) measurement performed for each cylinder at 816. From 818, the routine proceeds to each of 822, 832, and 842 to indicate degradation of an engine crankshaft based on the piston position of each cylinder (at 822), to indicate degradation of an engine camshaft based on the valve position of each cylinder (at 832), and/or to indicate misalignment of a crankshaft relative to a camshaft based on the piston and valve position measurements.

Specifically, at 822, the routine includes comparing the relative position of pistons between the engine cylinders (as determined at 818). For example, the piston position of a first cylinder may be determined and used to estimate the piston position of the remaining engine cylinders (e.g., based on their firing order and engine configuration).

As such, the relative position may be captured statically (as depicted) or dynamically. For example, if the laser is operated in the low energy mode while the engine is moving, light from the laser system may be reflected off the top of a cylinder piston, and the reflected light will have a different frequency relative to the initial light emitted. This detectable frequency shift is known as the Doppler Effect and has a known relation to the velocity of the piston if the piston is moving. Thus, the illumination measurement may be used to determine the position and velocity of the piston. In addition to using the positional information for identifying degradation, the position and velocity of the piston may also be used to coordinate the timing of ignition events and injection of the air/fuel mixture. For example, position information may be used to determine which cylinder fires first an engine restart from the idle-stop condition.

At 824, it may be determined if there is a discrepancy between the relative piston position of the cylinders. For example, the expected position of the cylinder pistons may be compared to actual estimated values. As such, based on the position of a piston in a given cylinder, the position of pistons in remaining cylinders of the engine may be inferred (e.g., based on cylinder firing order and cylinder configuration in the engine). Thus, the relative positions and the relative differences in piston positions may be calculated. If there is a deviation, at 826, crankshaft degradation may be indicated. In one example, crankshaft degradation may be indicated based on a difference between the piston position of a first cylinder relative to a second cylinder being higher than a threshold amount. Indicating degradation may include, for example, setting a diagnostic code to indicate that the crankshaft is twisted. In an alternate example, the controller may set a diagnostic code to indicate that the crankshaft is broken. In further examples, crankshaft degradation due to a twisted crankshaft may be differentiated from crankshaft degradation due to a broken crankshaft. As an example, if the crankshaft was broken, the position of at least some of the cylinders may not change. In comparison, if the crankshaft was twisted, all the cylinders would still be in motion but an unexpected offset may be observed between the timing/position of all the cylinders. If crankshaft degradation is not determined, the routine may end.

It will be appreciated that while the routine of FIG. 8 depicts the vehicle being in a non-combusting mode, this may not be a limiting condition. In some embodiments of the routine of FIG. 8, the various position-based diagnostic routines may be initiated while the vehicle is in a combusting mode. For example, crankshaft diagnostics may be performed while the engine is combusting so that the engine can be turned as part of the diagnostic routine so as to better differentiate a twisted crankshaft from a broken crankshaft.

At 832, the routine includes comparing the relative position of valves between the engine cylinders (as determined at 820). Since the cam (e.g., intake cam) position of each cylinder directly correlates with the corresponding valve (e.g., intake valve) position of each cylinder, the routine may additionally compare the relative cam position of the cylinders (as determined at 816). For example, the intake valve or intake cam position of a first cylinder may be determined and used to estimate the intake valve or intake cam position of the remaining engine cylinders (e.g., based on their firing order, engine configuration, and cylinder stroke). As such, the relative position may be captured statically or dynamically, as discussed above. In addition to using the positional information for identifying degradation, the valve or cam position measurement may also be used to coordinate the timing of ignition events and injection of the air/fuel mixture. For example, position information may be used to determine which cylinder fires first and which cylinder fuels first. For example, a cylinder with an intake valve open may be determined to be in an intake stroke and may receive fuel during an engine restart from the idle-stop condition.

At 834, it may be determined if there is a discrepancy between the relative cam or valve position of the cylinders. For example, the expected position of the cylinder valves or cams may be compared to actual estimated values. As such, based on the position of an intake valve in a given cylinder, the position of intake valves in remaining cylinders of the engine, as well as the position of exhaust valves in all the cylinders of the engine, may be inferred (e.g., based on cylinder firing order and cylinder configuration in the engine). Thus, the relative positions and the relative differences in valve or cam may be calculated. If there is a deviation, at 836, camshaft degradation may be indicated. In one example, camshaft degradation may be indicated based on a difference between the valve position of a first cylinder relative to a second cylinder being higher than a threshold amount. In another example, where the valves are independently actuated, it may be determined if the measured valve position of a given cylinder is where the valve position is expected to be. For example, it may be determined if the valve position indicates an open intake valve where the cylinder's intake valve has been actuated open. Alternatively, it may be determined if the valve position indicates a closed intake valve where the cylinder's intake valve has not been actuated open. Indicating degradation may include, for example, setting a diagnostic code to indicate that the camshaft is twisted or broken. In an alternate example, the controller may set a diagnostic code to indicate that an electric cam system coupled to the camshaft is degraded. In further examples, camshaft degradation due to a twisted camshaft may be differentiated from camshaft degradation due to a broken camshaft. As an example, if the camshaft was broken, at least some of the cylinders may have no cam event while others do. In comparison, if the camshaft was twisted, all the cylinders would have cam events but an unexpected offset may be observed between the cam event timing of all the cylinders. In the case of pure actuator systems having no shaft, the measure intake valve position would be compared to the commanded intake valve position for each cylinder to identify degradation. If camshaft degradation is not determined, the routine may end.

It will be appreciated that while the routine of FIG. 8 depicts the vehicle being in a non-combusting mode, this may not be a limiting condition. In some embodiments of the routine of FIG. 8, the various position-based diagnostic routines may be initiated while the vehicle is in a combusting mode. For example, camshaft diagnostics may be performed while the engine is combusting so that the engine can be turned as part of the diagnostic routine so as to better differentiate a twisted camshaft from a broken camshaft.

At 842, the routine includes comparing the relative position of the crankshaft with the position of the camshaft. As an example, the crankshaft position determined based on the piston position of the all the engine cylinders may be compared to the camshaft position determined based on the valve position of the engine cylinders. For example, the piston position for each cylinder, as determined at 814, may be compared to an intake valve position for the same given cylinder, as determined at 816. In addition, based on the piston position for the cylinder, a cylinder stroke, and thereby, a cylinder valve position may be estimated. The actual and expected values may then be compared. For example, the piston position of a first cylinder may be determined used to estimate the intake valve or intake cam position of the given first cylinder.

At 844, it may be determined if there is a discrepancy between the estimated valve position and the expected valve position, as determined based on the piston position. If there is a deviation, at 846, misalignment of the cylinder crankshaft relative to the camshaft may be indicated. For example, misalignment may be indicated based on a deviation of an estimated cylinder valve position from an expected valve position, wherein the expected valve position was based on an estimated piston position for the same cylinder. Herein, the cylinder valve position may be a cylinder intake valve position. As discussed above, the cylinder piston position is identified based on a time taken to detect a laser signal, generated at a laser ignition device of the engine, to be reflected off the cylinder piston while the cylinder valve position is identified based on a time taken to detect a laser signal, generated at the laser ignition device of the engine, to be reflected off the cylinder valve.

In another example, misalignment may be indicated based on a difference between the estimated crankshaft position and the estimated camshaft position being higher than a threshold amount. For example, based on the measured intake valve or intake cam position (e.g., based on the intake valve/cam, being at a home position) of all the engine cylinders, a camshaft position may be estimated (e.g., a camshaft home position may be determined). Then, based on the camshaft position, a crankshaft position correlating with the camshaft position may be determined. The engine may have a tolerance of up to a threshold amount of change of the crankshaft from the home position (e.g., up to 4 degrees). If the crankshaft position is shifted by more than 4 degrees, then misalignment may be determined. In response to the discrepancy, the controller may set a diagnostic code at 846. In response to the indication of misalignment, the controller may apply an offset to the cam position until the alignment of the shafts is restored.

In this way, illumination based positional measurements may be used to diagnose an engine camshaft, a cylinder crankshaft, cylinder intake valves, cylinder exhaust valves, and cylinder intake or exhaust cams.

Figure 9:
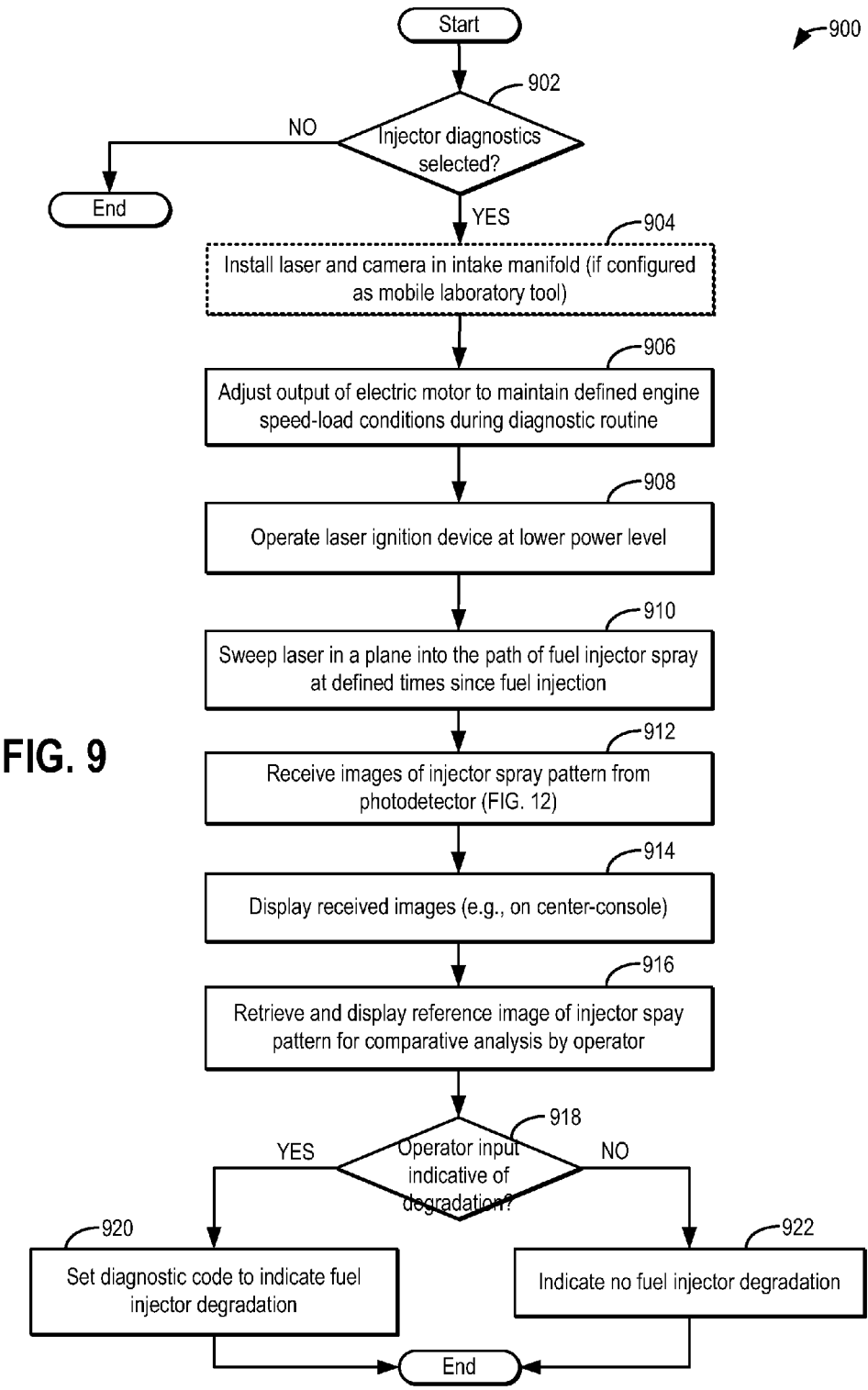
FIGS. 9-10 show an example fuel injector spray pattern diagnosis.

Now turning to FIG. 9, an example routine 900 is shown for injector spray pattern diagnostics. In one example, routine 900 may be diagnostic routine performed as part of the first diagnostic mode (Mode_1), as described at FIG. 6.

At 902, the routine includes confirming that injector diagnostics have been selected. For example, it may be confirmed that the engine is in the first diagnostic mode. Else the routine may end.

In some embodiments, the injector diagnostics may be performed using the laser system configured as a mobile tool. When in the mobile tool application, the routine includes, optionally at 904, installing the laser and the photodetector (e.g., the CCD camera) in the intake manifold of the engine. The positioning of the laser and the camera in the intake manifold may vary depending in whether the fuel injector being diagnosed is a direct fuel injector or a port fuel injector. For example, if the spray pattern of a direct fuel injector is being diagnosed, the laser and camera may be arranged in-line, such as in the location of the spark plug. In comparison, if the spray pattern of a port fuel injector is being diagnosed, the laser and camera may be arranged at an angle to each other, such as with the laser and the camera in the intake port in the line of the injector spray. It will be appreciated that the laser and the camera may both need to be in the line-of-sight with the injector spray pattern. In one example, this requirement may dictate having a second set of low power lasers in the intake ports for port injected engines.

At 906, the routine includes adjusting the output of an electric motor of the hybrid vehicle in which the engine is coupled so as to maintain a defined engine speed-load condition during the diagnostic routine. For example, the motor output may be adjusted to maintain a reference engine speed-load that was used during the last iteration (or all prior iterations) of the injector spray pattern diagnostic routine.

At 908, the routine includes operating the laser ignition device at the lower power level so as to direct laser pulses into the cylinder to planar sweep the cylinder during an intake stroke of the cylinder with laser pulses having a power sufficient for cylinder illumination but not sufficient for initiating cylinder combustion. At 910, the routine includes sweeping the laser in a plane into the path of the fuel injector spray at defined times since fuel injection by the fuel injector. For example, the laser may be fired in rapid succession to provide a planar sweep, or laser arc, across the path of the injector spray.

At 912, the controller may receive images captured by the photodetector (e.g., the CCD camera) during the laser operation. As such, the photodetector may have captured images using light generated by the laser operation in the lower power mode. The images may represent a conic section of the fuel injector spray pattern. Example fuel injector spray pattern images are shown and discussed with reference to FIG. 10. At 914, the images may be displayed to an operator, such as a service technician or mechanic. In one example, the images may be displayed on a display device on the center console of the vehicle. Alternatively, the images may be displayed on a display device coupled to the mobile diagnostic tool.

At 916, the controller may retrieve and display a reference image of an expected injector spray pattern. The reference image may be automatically retrieved and displayed based on the captured image (at 912) or based on the selection of the injector diagnostic routine (at 902). Alternatively, the reference image may be retrieved upon receiving input from the vehicle operator, such as via the (touch-interactive) display device. The reference image may include an image of the given fuel injector previously diagnosed at the given reference engine speed-load conditions wherein no injector degradation was determined. Alternatively, the reference image may include the image of a corresponding fuel injector (e.g., a similar port or direct fuel injector) previously diagnosed at the given reference engine speed-load conditions wherein no injector degradation was determined. In this way, the generated image and the reference image may be presented to the vehicle operator for comparative analysis.

Figure 10:
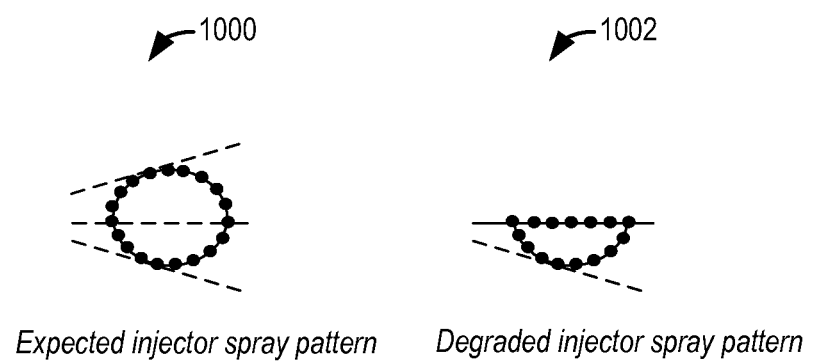

At 918, it may be determined if operator input has been received indicating injector degradation. For example, the operator may compare the generated image with the reference image to see if the injector spray pattern is as required to be. FIG. 10 shows example injector spray pattern images captured in the laser arc by a photodetector coupled to the laser system. At 1000, an expected spray pattern is shown. Specifically, 1000 may be a reference image representing a fuel injector spray pattern captured during the reference engine speed-load conditions while the injector was not degraded. In comparison, 1002, shows a degraded injector spray pattern. Since the spray cone at 1002 is not conically shaped (compare to conically shaped spray cone of 1000), and has part of the conic section missing or skewed, based on the images, an operator may be determine that the fuel injector is degraded. For example, the injector may be determined to be clogged.

If the operator input indicates degradation of the fuel injector, at 920, the controller may set a diagnostic code to indicate the degradation. The controller may also request fuel injector replacement. If no input is received, the controller may indicate at 922 that the fuel injector is not degraded. Optionally, if no degradation is determined, the controller may save the image captured during the given iteration of the fuel injector diagnostic routine in the controller's memory for use a reference image during a later iteration of the diagnostic routine.

Now turning to FIG. 11, an example routine 1100 for diagnosing cylinder airflow patterns is shown. In one example, routine 1100 may be a diagnostic routine performed as part of the first diagnostic mode (Mode_1), as described at FIG. 6. Furthermore, the diagnostic routine may be performed using the laser system configured as a mobile tool.

At 1102, the routine includes confirming that airflow diagnostics have been selected. For example, it may be confirmed that the engine is in the first diagnostic mode. Else the routine may end. At 1104, the routine includes presenting high humidity air into the air intake system. For example, a water spray may be injected or introduced into the air intake system (or directly into the intake manifold). In alternate examples, instead of high humidity air, smoke may be presented to the air intake system of the engine.

At 1106, the routine includes operating the laser in the lower power mode. As discussed previously, the laser system is operated to direct laser pulses into the cylinder to planar sweep the cylinder during an intake stroke of the cylinder with laser pulses having a power sufficient for cylinder illumination but not sufficient for initiating cylinder combustion. At 1108, the routine includes sweeping the laser in a plane into the path of cylinder airflow at defined times since intake valve opening (IVO). For example, the laser may be fired in rapid succession to provide a planar sweep across the cylinder during the intake stroke.

In some examples, a swirl control valve or charge motion control valve in the intake port, upstream of the intake valve, may be operated during the introduction of the humid air or smoke so as to accentuate the swirling motion of the airflow received in the cylinder during the intake stroke.

At 1110, the controller may receive images captured by the photodetector (e.g., the CCD camera) during the laser operation. As such, the photodetector may have captured images using light generated by the laser operation in the lower power mode. The images may represent airflow patterns in the cylinder. Specifically, the camera and laser scan may illuminate the airflow pattern by viewing the water vapor (from the high humidity air) condensing in the cylinder as it encounters low pressure during the intake stroke.

At 1112, the captured images may be displayed to an operator, such as a service technician or mechanic. In one example, the images may be displayed on a display device on the center console of the vehicle. Alternatively, the images may be displayed on a display device coupled to the mobile diagnostic tool.

At 1114, the controller may retrieve and display one or more reference images of an expected cylinder airflow pattern. The reference image may be automatically retrieved and displayed based on the captured image (at 1110) or based on the selection of the airflow diagnostic routine (at 1102). Alternatively, the reference image may be retrieved upon receiving input from the vehicle operator, such as via the (touch-interactive) display device. The reference image may include an image of airflow pattern captured previously when no intake valve or airflow degradation was determined. Optionally, the reference image may have been captured while operating the engine at a reference engine speed-load condition, or the same engine speed-load condition at which the images were currently captured. As such, in the absence of airflow degradation (such as due to intake valve degradation), the introduced humid air or smoke may generate a helical pattern in the cylinder due to the interaction of the humid air or smoke with the low pressure encountered in the cylinder during the intake stroke. Thus, the reference image may include a helical pattern, such as a swirl or circle. In this way, the generated image and the reference image may be presented to the vehicle operator for comparative analysis.

At 1116, it may be determined if operator input has been received indicating airflow degradation. For example, the operator may compare the generated image with the reference image to see if the airflow pattern is helical, as required to be. If the captured image depicts turbulence in random parts of the cylinder, the operator may infer and indicate that airflow in the cylinder is degraded. If the operator input indicates degradation of cylinder airflow, at 1118, the controller may set a diagnostic code to indicate the degradation of airflow due to possible degradation of the intake valve. For example, the controller may indicate that there is potential build-up of material on the intake valve. Alternatively, the controller may indicate that the swirl control valve is degraded. The controller may accordingly request control actions be performed, such as advancing the intake cam timing to compensate for the degraded flow through the valve. If no input is received, the controller may indicate at 1120 that the airflow (and therefore the intake valve) is not degraded. Optionally, if no degradation is determined, the controller may save the image captured during the given iteration of the airflow diagnostic routine in the controller's memory for use a reference image during a later iteration of the diagnostic routine.

Figure 12:
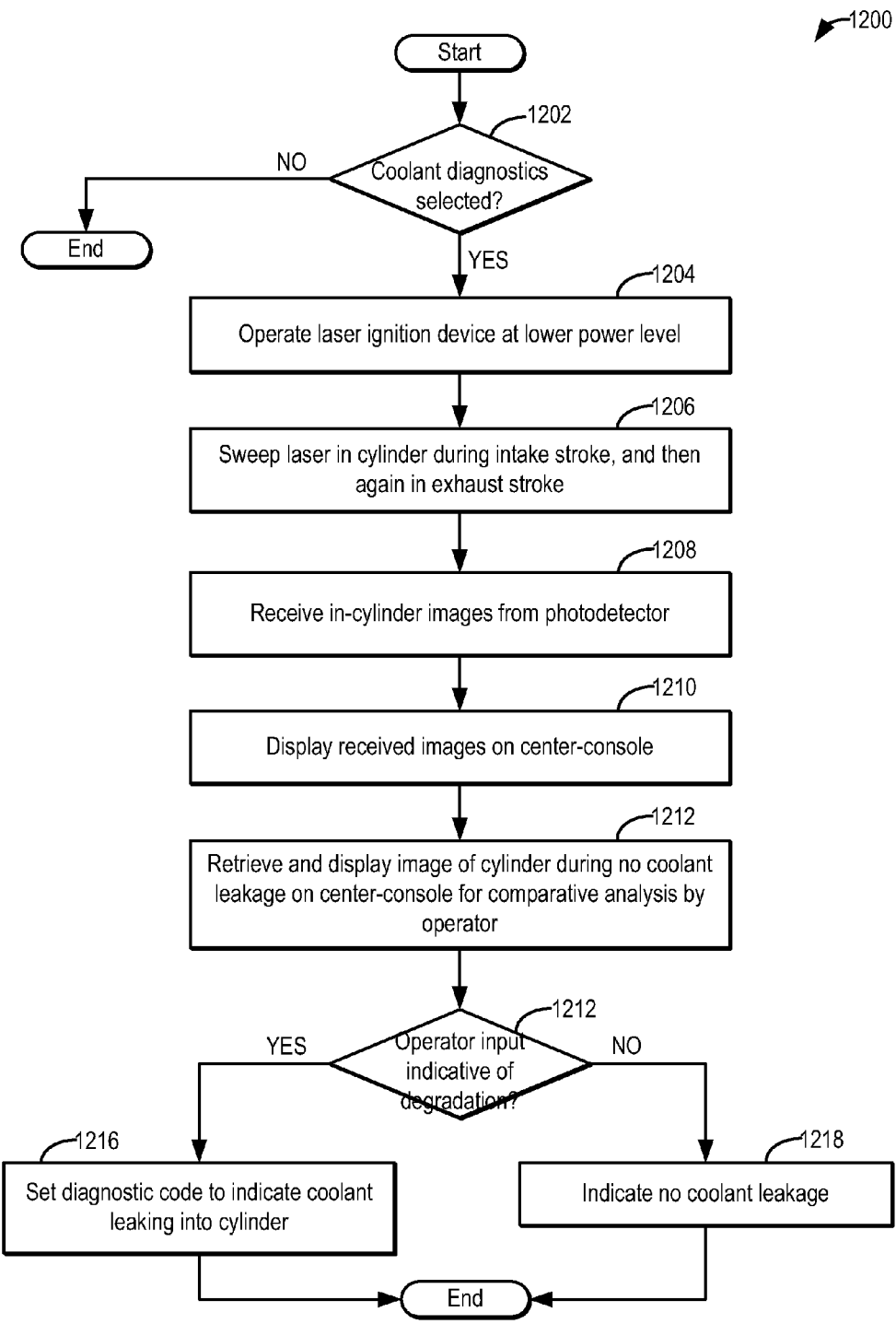

Now turning to FIG. 12, an example routine 1200 for diagnosing coolant leakage into a cylinder is shown. In one example, routine 1200 may be a diagnostic routine performed as part of the first diagnostic mode (Mode_1), as described at FIG. 6. Furthermore, the diagnostic routine may be performed using the laser system configured as a mobile tool.

At 1202, the routine includes confirming that coolant flow diagnostics have been selected. For example, it may be confirmed that the engine is in the first diagnostic mode. Else the routine may end. At 1204, the routine includes operating the laser in the lower power mode. As discussed previously, the laser system is operated to direct laser pulses into the cylinder having a power sufficient for cylinder illumination but not sufficient for initiating cylinder combustion. At 1206, the routine includes using the laser pulses to planar sweep the cylinder during an intake stroke of the cylinder. Additionally, at 1206, the routine includes operating the laser in the lower power mode to planar sweep the cylinder again, after cylinder combustion, during an exhaust stroke of the given cycle of the cylinder. For example, the laser may be swept into the cylinder at defined times since intake valve opening (IVO) and before exhaust valve closing (EVC). For example, the laser may be fired in rapid succession to provide a planar sweep across the cylinder during the intake stroke and the exhaust stroke.

At 1208, the controller may receive images captured by the photodetector (e.g., the CCD camera) during the laser operation. As such, the photodetector may have captured images using light generated by the laser operation in the lower power mode. The images captured in the intake stroke may represent presence or absence of coolant entry into the cylinder during the intake stroke following an intake valve opening event. The images captured in the exhaust stroke may represent presence or absence of white smoke in the exhaust of the cylinder following combustion of any leaked coolant.

At 1210, the captured images may be displayed to an operator, such as a service technician or mechanic. In one example, the images may be displayed on a display device on the center console of the vehicle. Alternatively, the images may be displayed on a display device coupled to the mobile diagnostic tool.

At 1212, the controller may retrieve and display one or more reference images of an expected cylinder airflow pattern. The reference image may be automatically retrieved and displayed based on the captured image (at 1208) or based on the selection of the coolant flow diagnostic routine (at 1202). Alternatively, the reference image may be retrieved upon receiving input from the vehicle operator, such as via the (touch-interactive) display device. The reference image may include an image of expected coolant flow and exhaust smoke generation captured previously when no coolant leakage into the given cylinder was determined. Optionally, the reference image may have been captured while operating the engine at a reference engine speed-load condition, or the same engine speed-load condition at which the images were currently captured. As such, in the presence of coolant entry, coolant flow or vapors may be seen entering the cylinder from the bottom of the piston during the intake stroke. The coolant may then be seen generating excess white smoke in the exhaust stroke, due to combustion of the coolant during the cylinder combustion event. In this way, the generated image and the reference image may be presented to the vehicle operator for comparative analysis.

At 1214, it may be determined if operator input has been received indicating coolant entry. For example, the operator may compare the generated image with the reference image to see if coolant has leaked into the cylinder. If the operator input indicates degradation of cylinder airflow, at 1216, the controller may set a diagnostic code to indicate the degradation of coolant flow and leakage of coolant into the cylinder due to possible degradation of the piston rings. If no input is received, the controller may indicate at 1218 that the coolant flow (and therefore the cylinder piston ring) is not degraded. Optionally, if no degradation is determined, the controller may save the image captured during the given iteration of the coolant flow diagnostic routine in the controller's memory for use a reference image during a later iteration of the diagnostic routine.

Figure 13:
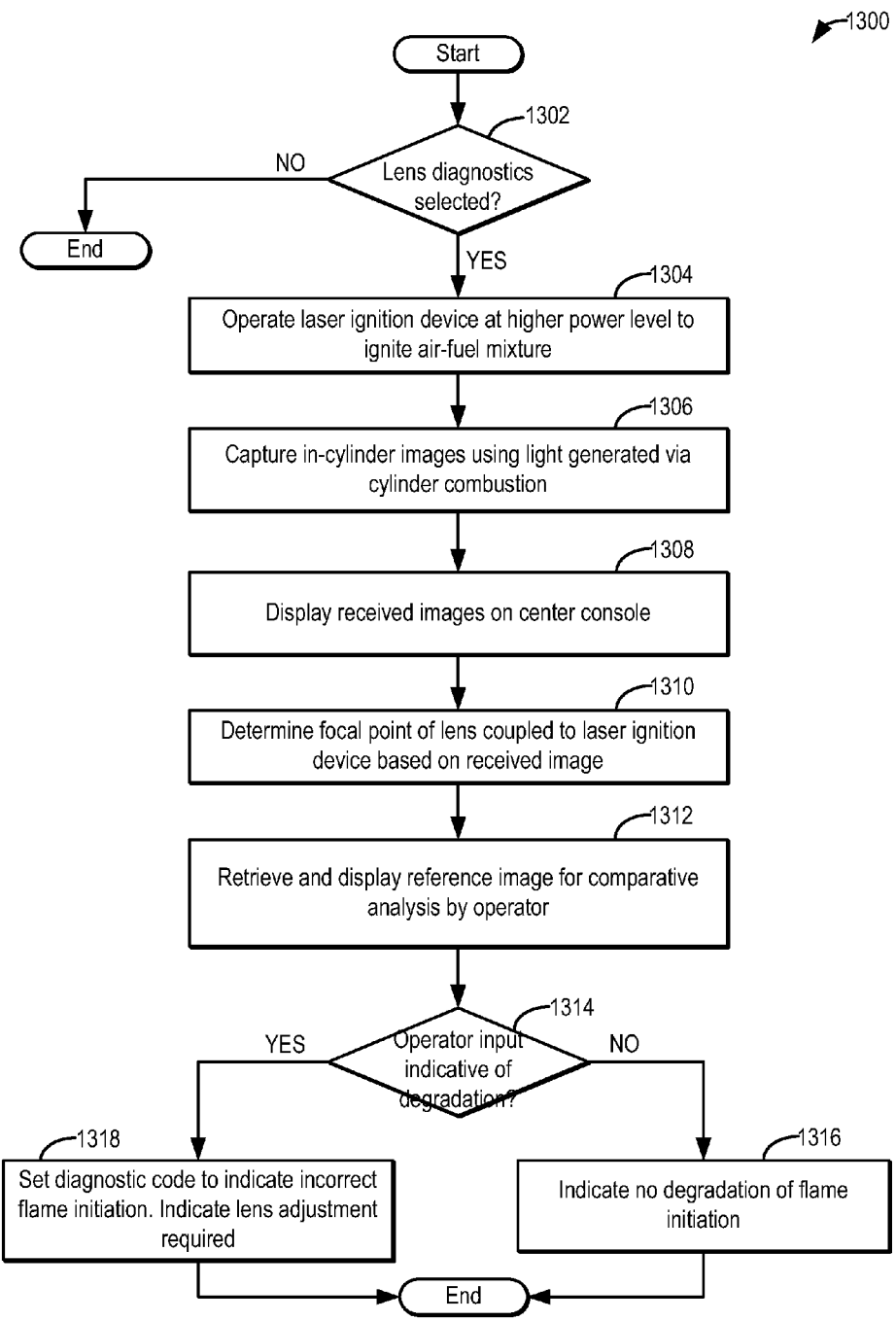

Now turning to FIG. 13, an example routine 1300 for diagnosing a converging lens coupled to the laser system of a cylinder is shown. In one example, routine 1300 may be a diagnostic routine performed as part of the second diagnostic mode (Mode_2), as described at FIG. 7. Furthermore, the diagnostic routine may be performed using the laser system configured as a mobile tool.

At 1302, the routine includes confirming that lens diagnostics have been selected. For example, it may be confirmed that the engine is in the second diagnostic mode. Else the routine may end. At 1304, the routine includes operating the laser in the higher power mode. As discussed previously, the laser system is operated to direct laser pulses into the cylinder having a sufficient for initiating cylinder combustion and more power than required only for cylinder illumination. The laser pulses may also be used to planar sweep the cylinder during a compression stroke of the cylinder.

At 1306, the controller may capture in-cylinder images, via the photodetector of the laser system, using light generated during cylinder combustion. At 1308, the controller may receive images captured by the photodetector (e.g., the CCD camera) during the laser operation. As such, the photodetector may have captured images using light generated during cylinder combustion. The images may represent the flame front during the cylinder combustion event. At 1308, the captured images may be displayed to an operator, such as a service technician or mechanic. In one example, the images may be displayed on a display device on the center console of the vehicle. Alternatively, the images may be displayed on a display device coupled to the mobile diagnostic tool.

At 1310, based on the captured images, a location of flame initiation may be determined. For example, based on the intensity of the captured images, a location on the piston surface or cylinder wall where the flame front initiated may be determined. As such, since the flame is initiated via laser ignition, and further since the laser system uses a converging lens to direct the laser pulse into the cylinder for combustion initiation, the location of flame initiation may also correlate with the focal point of the lens. Thus, based on the received image, the controller may determine the focal point of the lens coupled to the laser system.

At 1312, the controller may retrieve and display one or more reference images of an expected flame front initiation and progression. The reference image may be automatically retrieved and displayed based on the captured image (at 1306) or based on the selection of the lens diagnostic routine (at 1302). Alternatively, the reference image may be retrieved upon receiving input from the vehicle operator, such as via the (touch-interactive) display device. The reference image may include an image of expected flame front initiation and progression. Optionally, the reference image may have been captured while operating the engine at a reference engine speed-load condition, or the same engine speed-load condition at which the images were currently captured. As such, if the lens is misaligned, the location of flame initiation may be skewed to a side, and may not correlate with the expected location of flame initiation. Thus, the generated image and the reference image may be presented to the vehicle operator for comparative analysis.

At 1314, it may be determined if operator input has been received indicating lens misalignment or incorrect location of flame initiation. For example, the operator may compare the generated image with the reference image to see if the flame initiated towards an edge of the cylinder. If the operator input indicates degradation of flame initiation, at 1316, the controller may set a diagnostic code to indicate the degradation of flame initiation due to possible misalignment of the laser system lens. The controller may further indicate that lens adjustment (e.g., realignment) is required. If no input is received, the controller may indicate at 1318 that the flame initiation, and lens arrangement is not degraded. Optionally, if no degradation is determined, the controller may save the image captured during the given iteration of the lens diagnostic routine in the controller's memory for use a reference image during a later iteration of the diagnostic routine.

It will be appreciated that in still further examples, one or more of the above described routines may be adjusted to keep the lens of the laser ignition system clean. As an example, the camera lens may be located relatively high on the side of the cylinder where the piston ring may clean the lens. Additionally, the laser could burn off residual soot. As such, this approach may require either a shutter or may need a direct line of laser sight blocked to avoid damaging the photodetector (such as the CCD camera).

As another example, the camera (or photodetector) and the laser may be configured to share a lens. Therein, regular laser operation may burn off anything covering the lens, thereby cleaning the lens during laser operation.

In this way, a laser ignition system may be advantageously used to diagnose various cylinder components and conditions. By using the laser to illuminate the cylinder and the photodetector to capture in-cylinder images using laser illumination, a visual inspection of the cylinder can be performed without the need for bore-scopes, engine tear down, or other labor, cost, and time-intensive approaches. By enabling a mechanic to see the images of the interior of the cylinder, along with relevant reference images of the same cylinder, the engine health may be diagnosed more accurately and reliably by the mechanic. By using existing engine hardware to perform the visual inspection, component and cost reduction benefits are achieved. Overall, engine inspection can be simplified without reducing inspection accuracy.

Note that the example control and estimation routines included herein can be used with various engine and/or vehicle system configurations. The control methods and routines disclosed herein may be stored as executable instructions in non-transitory memory. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method for an engine, comprising:
over an engine cycle,
operating a laser ignition device in each engine cylinder;
identifying a piston position in each cylinder based on the operating; and
differentiating between a twisted crankshaft and a broken crankshaft based on the piston position of each cylinder.

2. The method of claim 1, wherein identifying a piston position in each cylinder based on the operating includes:
for each cylinder,
sensing light reflected off a top surface of the piston; and
estimating the piston position based on a time elapsed between the operating of the laser ignition device and the sensing of the light.

3. The method of claim 1, wherein the operating includes operating the laser ignition device at a lower power in one of a compression stroke, a power stroke, and an exhaust stroke of each engine cylinder to identify the piston position, the lower power below a threshold power required to initiate cylinder combustion.

4. The method of claim 1, further comprising operating the laser ignition device at a higher power in a compression stroke of each cylinder to initiate cylinder combustion, the higher power above a threshold power required to only illuminate the cylinder.

5. The method of claim 1, wherein the differentiating includes indicating that the crankshaft is twisted based on a difference between the piston position of a first cylinder relative to a second cylinder being higher than a threshold amount, the second cylinder selected based on the first cylinder.

6. The method of claim 1, wherein the differentiating includes indicating that the crankshaft is broken based on the piston position of at least some cylinders of the engine not changing.

7. A method for an engine, comprising:
over an engine cycle,
operating a laser ignition device in each engine cylinder;
identifying a cylinder valve position in each cylinder based on the operating; and
differentiating between a twisted camshaft and a broken camshaft based on the valve position of each cylinder.

8. The method of claim 7, wherein the cylinder valve is a cylinder intake valve.

9. The method of claim 8, wherein identifying a valve position in each cylinder based on the operating includes:
for each cylinder,
sensing light reflected off the cylinder valve; and
estimating a camshaft position based on a time elapsed between the operating of the laser ignition device and the sensing of the light.

10. The method of claim 7, wherein the operating includes operating the laser ignition device at a lower power in one of an intake stroke or an exhaust stroke of each engine cylinder, the lower power below a threshold power required to initiate cylinder combustion.

11. The method of claim 10, further comprising operating the laser ignition device at a higher power in a compression stroke of each cylinder to initiate cylinder combustion, the higher power above a threshold power required to only illuminate the cylinder.

12. The method of claim 9, wherein the indicating includes indicating camshaft degradation based on a difference between the valve position of a first cylinder and a second cylinder being higher than a threshold amount, the second cylinder selected based on the first cylinder.

13. The method of claim 7, wherein the differentiating includes:
indicating that the camshaft is twisted based on each cylinder having a cam event and a cam event timing of all the cylinders having an unexpected offset; and
indicating the camshaft is broken based on some cylinders having no cam event while remaining cylinders have the cam event.

14. The method of claim 7, wherein indicating degradation of the camshaft includes indicating that an electric cam system coupled to the camshaft is degraded.

15. A method, comprising:
operating a laser ignition device in an engine cylinder over an engine cycle;
identifying a cylinder piston position and a cylinder valve position based on the operating, the piston position identified during a compression, power, or exhaust stroke of the engine cycle based on a reflected laser signal, the cylinder valve position identified during an intake stroke of the engine cycle based on a blocked laser signal; and
indicating misalignment of a crankshaft relative to a camshaft based on a deviation of the identified cylinder valve position from an expected valve position, the expected valve position based on the identified cylinder piston position.

16. The method of claim 15, wherein the cylinder valve position includes a cylinder intake valve position.

17. The method of claim 16, wherein the identifying includes:
identifying the cylinder valve position based on a time taken to detect a laser signal reflected off of a cylinder valve, the cylinder valve substantially blocking the laser signal; and
identifying the cylinder piston position based on a time taken to detect a laser signal reflected off the cylinder piston.

18. The method of claim 15, wherein operating the laser ignition device includes operating at a power level lower than a threshold power required for initiating cylinder combustion.

19. The method of claim 16, wherein indicating misalignment includes setting a diagnostic code, and in response to the indication, advancing an intake cam timing to compensate for degraded flow through the cylinder intake valve.

* * * * *